(12) United States Patent
Van Den Bogart et al.

(10) Patent No.: US 8,251,969 B2
(45) Date of Patent: Aug. 28, 2012

(54) BODY ADHERING ABSORBENT ARTICLE

(75) Inventors: Thomas William Van Den Bogart, Slinger, WI (US); Adrienne Rae Loyd, Neenah, WI (US); David-John Enz, Neenah, WI (US); Carmen Lira-Núñez, Appleton, WI (US); Suzanne K. Sullivan Conrad, Combined Locks, WI (US); Roxanne Belinda Hallock, Oshkosh, WI (US); Deborah Snell Hannah, Appleton, WI (US); Candace Dyan Krautkramer, Neenah, WI (US); Mary L. McDaniel, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 770 days.

(21) Appl. No.: 11/890,093

(22) Filed: Aug. 3, 2007

(65) Prior Publication Data

US 2009/0036858 A1  Feb. 5, 2009

(51) Int. Cl.
*A61F 13/15* (2006.01)
*A61F 13/20* (2006.01)

(52) U.S. Cl. .................. 604/386; 604/385.17; 604/387; 604/401

(58) Field of Classification Search ............. 604/385.17, 604/385.18, 386, 387, 401, 307
See application file for complete search history.

(56) References Cited

U.S. PATENT DOCUMENTS

| | | | |
|---|---|---|---|
| 2,842,897 A | 7/1958 | Finn | |
| 3,288,346 A | 11/1966 | Peppler | |
| 3,338,992 A | 8/1967 | Kinney | |
| 3,341,394 A | 9/1967 | Kinney | |
| 3,502,538 A | 3/1970 | Petersen | |
| 3,502,763 A | 3/1970 | Hartmann | |
| 3,542,615 A | 11/1970 | Dobo et al. | |
| 3,692,618 A | 9/1972 | Dorschner et al. | |
| 3,802,817 A | 4/1974 | Matsuki et al. | |
| 3,849,241 A | 11/1974 | Butin et al. | |
| 3,963,029 A | 6/1976 | Brooks | |
| 3,972,328 A | 8/1976 | Chen | |
| 4,072,151 A | 2/1978 | Levine | |
| 4,340,563 A | 7/1982 | Appel et al. | |
| 4,488,928 A | 12/1984 | Ali Khan et al. | |
| 4,505,976 A | 3/1985 | Doehnert et al. | |
| 4,631,062 A | 12/1986 | Lassen et al. | |

(Continued)

FOREIGN PATENT DOCUMENTS

DE   692 32 589 T2   12/2002

(Continued)

OTHER PUBLICATIONS

American Society for Testing Materials (ASTM) Designation: D1300-53 T, "Tentative Specifications and Methods of Test for Laminated Thermosetting Decorative Sheets," pp. 148-166, issued 1953.

(Continued)

*Primary Examiner* — Melanie Hand
(74) *Attorney, Agent, or Firm* — David J. Arteman; Randall W. Fieldhack

(57) ABSTRACT

The present invention provides a body adhering absorbent articles which is capable of absorbing bodily fluids. In particular embodiment of the present invention, provided is an absorbent article which is specifically designed for attachment to a wearer's skin in the vulva region of the wearer's torso.

26 Claims, 12 Drawing Sheets

U.S. PATENT DOCUMENTS

| | | | |
|---|---|---|---|
| 4,673,403 A | 6/1987 | Lassen et al. | |
| 4,743,245 A | 5/1988 | Lassen et al. | |
| 4,781,712 A | 11/1988 | Barabino et al. | |
| 4,798,603 A | 1/1989 | Meyer et al. | |
| 4,804,380 A | 2/1989 | Lassen et al. | |
| 4,846,824 A | 7/1989 | Lassen et al. | |
| 4,909,244 A | 3/1990 | Quarfoot et al. | |
| 4,977,892 A | 12/1990 | Ewall | |
| 5,051,259 A | 9/1991 | Olsen et al. | |
| 5,147,938 A | 9/1992 | Kuller | |
| 5,194,299 A | 3/1993 | Fry | |
| 5,194,550 A | 3/1993 | Rance et al. | |
| 5,221,275 A | 6/1993 | Van Iten | |
| 5,277,954 A | 1/1994 | Carpenter et al. | |
| 5,369,155 A | 11/1994 | Asmus | |
| 5,382,400 A | 1/1995 | Pike et al. | |
| 5,387,208 A | 2/1995 | Ashton et al. | |
| 5,419,956 A | 5/1995 | Roe | |
| 5,618,282 A | 4/1997 | Schlangen | |
| 5,632,736 A | 5/1997 | Block | |
| 5,662,633 A | 9/1997 | Doak et al. | |
| 5,669,894 A | 9/1997 | Goldman et al. | |
| 5,706,950 A | 1/1998 | Houghton et al. | |
| 5,714,225 A | 2/1998 | Hansen et al. | |
| 5,800,417 A | 9/1998 | Wood et al. | |
| 5,811,116 A | 9/1998 | Gilman et al. | |
| 5,830,202 A | 11/1998 | Bogdanski et al. | |
| 5,897,546 A | 4/1999 | Kido et al. | |
| 5,910,125 A | 6/1999 | Cummings et al. | |
| 5,994,613 A | 11/1999 | Cummings et al. | |
| 6,080,139 A | 6/2000 | Gallegos | |
| 6,255,552 B1 | 7/2001 | Cummings et al. | |
| 6,336,935 B1 | 1/2002 | Davis et al. | |
| 6,352,528 B1 | 3/2002 | Weber et al. | |
| 6,362,389 B1 | 3/2002 | McDowall et al. | |
| 6,386,203 B1 | 5/2002 | Hammerslag | |
| 6,495,229 B1 | 12/2002 | Carte et al. | |
| 6,566,575 B1 | 5/2003 | Stickels et al. | |
| 6,582,411 B1 | 6/2003 | Carstens et al. | |
| 6,617,490 B1 | 9/2003 | Chen et al. | |
| 6,632,210 B1 | 10/2003 | Glasgow et al. | |
| 6,657,009 B2 | 12/2003 | Zhou | |
| 6,659,990 B1 | 12/2003 | Odorzynski et al. | |
| 6,670,402 B1 | 12/2003 | Lee et al. | |
| 6,733,483 B2 | 5/2004 | Raufman et al. | |
| 6,756,520 B1 | 6/2004 | Krzysik et al. | |
| 6,803,420 B2 | 10/2004 | Cleary et al. | |
| 6,997,915 B2 * | 2/2006 | Gell et al. | 604/385.16 |
| 7,033,342 B2 | 4/2006 | Mizutani et al. | |
| 7,045,559 B2 | 5/2006 | Yahiaoui et al. | |
| 7,053,131 B2 | 5/2006 | Ko et al. | |
| 7,122,022 B2 | 10/2006 | Drevik | |
| 7,125,401 B2 | 10/2006 | Yoshimasa | |
| 7,137,971 B2 | 11/2006 | Tanzer | |
| 7,198,689 B2 | 4/2007 | Van Gompel et al. | |
| 7,217,259 B2 | 5/2007 | McDaniel | |
| 7,265,158 B2 | 9/2007 | Risen, Jr. et al. | |
| 7,358,282 B2 | 4/2008 | Krueger et al. | |
| 7,378,450 B2 | 5/2008 | Erkey et al. | |
| 7,918,837 B2 | 4/2011 | Rosenfeld | |
| 2001/0025163 A1 | 9/2001 | Brown et al. | |
| 2001/0039407 A1 | 11/2001 | Widlund | |
| 2002/0072725 A1 | 6/2002 | Falk | |
| 2002/0193766 A1 | 12/2002 | Gell et al. | |
| 2003/0004484 A1 | 1/2003 | Hammons et al. | |
| 2003/0078554 A1 | 4/2003 | Drevik | |
| 2003/0106825 A1 | 6/2003 | Molina et al. | |
| 2003/0208112 A1 | 11/2003 | Schmidt et al. | |
| 2004/0116883 A1 | 6/2004 | Krautkramer et al. | |
| 2004/0122385 A1 | 6/2004 | Morman et al. | |
| 2004/0151930 A1 | 8/2004 | Rouns et al. | |
| 2004/0167488 A1 * | 8/2004 | Bellucci et al. | 604/384 |
| 2004/0167491 A1 | 8/2004 | Mizutani | |
| 2004/0209075 A1 | 10/2004 | Maloney | |
| 2005/0010185 A1 * | 1/2005 | Mizutani et al. | 604/385.03 |
| 2005/0014901 A1 | 1/2005 | Osae et al. | |
| 2005/0059918 A1 | 3/2005 | Sigurjonsson et al. | |
| 2005/0124948 A1 * | 6/2005 | Morman et al. | 604/367 |
| 2005/0124960 A1 | 6/2005 | Ruman | |
| 2005/0136023 A1 | 6/2005 | Yahiaoui et al. | |
| 2005/0136077 A1 | 6/2005 | Yahiaoui et al. | |
| 2005/0137549 A1 | 6/2005 | Lindsay et al. | |
| 2005/0148984 A1 | 7/2005 | Lindsay et al. | |
| 2005/0182378 A1 | 8/2005 | Bonelli et al. | |
| 2005/0261652 A1 | 11/2005 | Digiacomantonio et al. | |
| 2006/0058760 A1 | 3/2006 | Rosenfeld et al. | |
| 2006/0063322 A1 | 3/2006 | Hsu et al. | |
| 2006/0079823 A1 | 4/2006 | Utterberg et al. | |
| 2006/0089613 A1 | 4/2006 | Mizutani et al. | |
| 2006/0129114 A1 | 6/2006 | Mason et al. | |
| 2006/0148917 A1 | 7/2006 | Radwanski et al. | |
| 2006/0188940 A1 | 8/2006 | Cima et al. | |
| 2006/0195053 A1 | 8/2006 | Oelund et al. | |
| 2006/0206077 A1 | 9/2006 | Warren et al. | |
| 2006/0224134 A1 | 10/2006 | Luizzi et al. | |
| 2006/0264884 A1 | 11/2006 | Carstens | |
| 2007/0124850 A1 | 6/2007 | Buettner | |
| 2007/0250028 A1 | 10/2007 | Woltman et al. | |
| 2007/0287973 A1 | 12/2007 | Cohen et al. | |
| 2008/0015535 A1 * | 1/2008 | Gannon et al. | 604/385.03 |
| 2008/0021424 A1 | 1/2008 | Erdman | |
| 2008/0057811 A1 | 3/2008 | Yahiaoui et al. | |
| 2008/0207779 A1 | 8/2008 | Yahiaoui et al. | |
| 2008/0234647 A1 | 9/2008 | Arterburn | |
| 2009/0071862 A2 | 3/2009 | Snell | |
| 2010/0121304 A1 | 5/2010 | Zhou et al. | |
| 2011/0092945 A1 | 4/2011 | Carstens | |

FOREIGN PATENT DOCUMENTS

| | | |
|---|---|---|
| EP | 0 909 662 A2 | 4/1999 |
| EP | 0 609 236 B1 | 5/2002 |
| KR | 10-2001-0022000 A | 3/2001 |
| KR | 10-0563880 B1 | 3/2006 |
| WO | WO 93/07841 A1 | 4/1993 |
| WO | WO 98/47454 A1 | 10/1998 |
| WO | WO 99/30659 A1 | 6/1999 |
| WO | WO 2006/028612 A1 | 3/2006 |

OTHER PUBLICATIONS

"Antiperspirant Drug Products for Over-the-Counter Human Use: Final Monograph," Final Rule, Federal Register—Rules and Regulations, vol. 68, No. 110, Jun. 9, 2003, pp. 34273-34293.

Berner, G. et al. "Photoinitiators—An Overview", Journal of Radiation Curing, vol. 6, No. 2, Apr. 1979, pp. 2-9.

Mahdavi, Alborz et al., "A Biodegradable and Biocompatible Gecko-Inspired Tissue Adhesive," PNAS, vol. 105, No. 7, Feb. 19, 2008, pp. 2307-2312.

* cited by examiner

BODY ADHERING ABSORBENT ARTICLE

FIELD OF THE INVENTION

The present invention relates generally to an absorbent article for absorbing bodily fluids.

BACKGROUND OF THE INVENTION

Absorbent personal care articles intended to absorb discharged body fluids are well known in the art. Such absorbent articles generally comprise a fibrous mass or other absorbent core which can absorb and hold body fluids. Similarly, it is well known that feminine care articles have been employed to absorb and hold liquids, such as urine and/or menses. A typical structure of an absorbent article includes a fluid impermeable back sheet, a fluid permeable top sheet and an absorbent core positioned between the back sheet and the top sheet. Prior absorbent articles have also included various other features to improve fluid handling, such as intake layers, distribution layers, retention layers and the like. In these absorbent personal care articles, the top sheet is the body-facing side of the absorbent article and the back sheet is the garment-facing side of the absorbent article.

Generally, the absorbent articles are held into place during use by using the wearer's waist and elastic materials in the waist portion of the absorbent product in place during use, in the case of pant-like garments, such as diapers and training pants, or by attaching the absorbent to the underwear or undergarment of a user, in the case of pads or liners. Current methods of attaching the absorbent article to the underwear or undergarment of a user include placing an adhesive on the garment-facing side of the back sheet, having flaps (wings) extend from the longitudinal sides of the absorbent article which wrap around the crotch portion of the underwear or undergarment of the user and a combination of the adhesive and the flaps.

It has also been suggested to use an adhesive to adhere the absorbent article to the skin of the user. However, the design of these absorbent articles was essentially the same as the absorbent articles which were attached to the underwear or undergarment of the user. That is, the adhesive is applied to the body-facing surface of the top sheet. Alternatively, in another design, a portion of the back sheet was wrapped around and over the top sheet. This portion of the back sheet which is wrapped around and over the top sheet becomes a body facing surface. An adhesive is applied to the portion of the back sheet which is wrapped over the top sheet. While these designs were effective for adhering the absorbent article to the skin of a user, these absorbent articles were not comfortable for users to wear, since the shape and size of the absorbent articles were the same as those absorbent articles which were attached to the undergarment or underwear of the user.

Similarly, absorbent articles that are attached to the underwear or undergarment of a user can also be uncomfortable for the user. This is because during normal movement of the body, portions of the body place opposed forces on the undergarment, which may cause the undergarment to be bunched or twisted. When this occurs, any absorbent article attached to the underwear or undergarment may also become bunched or twisted, causing discomfort to the wearer of the absorbent article. For example, the presence and absence of pressure from the absorbent article on the inner thighs as the user moves, which is often described by users as feeling "like a diaper", is one source which compromises comfort for users of conventional absorbent articles, including ultra-thin absorbent pads. In addition, the movement of the user may also cause the absorbent article to have a poor fit against the body of the user, which could result in leaks from the absorbent article.

Another disadvantage of conventional absorbent articles is that the silhouette or outline of the absorbent article may be visible to others through the clothing of the user. Even currently available ultra-thin absorbent articles may be visible through tight fitting outer clothing of a user. Therefore, conventional absorbent personal care articles do not always provide discretion for users.

There is a need in the art to provide users of absorbent articles with a discrete absorbent product, which is comfortable to wear and will effectively prevent or reduce premature leakage from the absorbent article.

SUMMARY OF THE INVENTION

Generally stated, the present invention provides a body-adhering absorbent article which is capable of absorbing bodily fluids.

In one embodiment of the present invention, an absorbent article for attachment to a wearer's skin in the vulva region of the wearer's torso is provided. The absorbent article has a shell having a first side and a second side, the first side having a first area and a second area. The first area surrounds the majority of the second area. Located within the second area is an absorbent structure containing an absorbent material. In this embodiment, the first area of the shell is designed to attach and/or adhere to the wearer's skin surrounding the vulva region of the female torso, when the absorbent article is applied to the wearer. The shell is sized and shaped such that the extent of the first area of the shell only contacts the skin proximate to the vulva of the wearer, and may attach to the pubic and/or the perineal regions of the body of the user.

In another embodiment of the present invention, provided is an absorbent article for attachment to a wearer's skin in the vulva region of the wearer's torso. This absorbent article has a three-dimensional concave shape that the first side of the shell is an inward curving surface. Attached to the shell or integrated with the shell is an absorbent structure.

The absorbent articles of the present invention may be used as a pantiliner, a sanitary napkin or an incontinence absorbent product. In addition, the absorbent article may be worn as an underwear substitute since the absorbent article does not need underwear hold the absorbent article in place. As an underwear substitute, the absorbent article provides protection to the vulva area by creating a barrier between the clothing and the vulva.

By providing the disposal absorbent article of the present invention, drawbacks of the conventional absorbent personal care articles are minimized.

DEFINITIONS

Figure 1A:
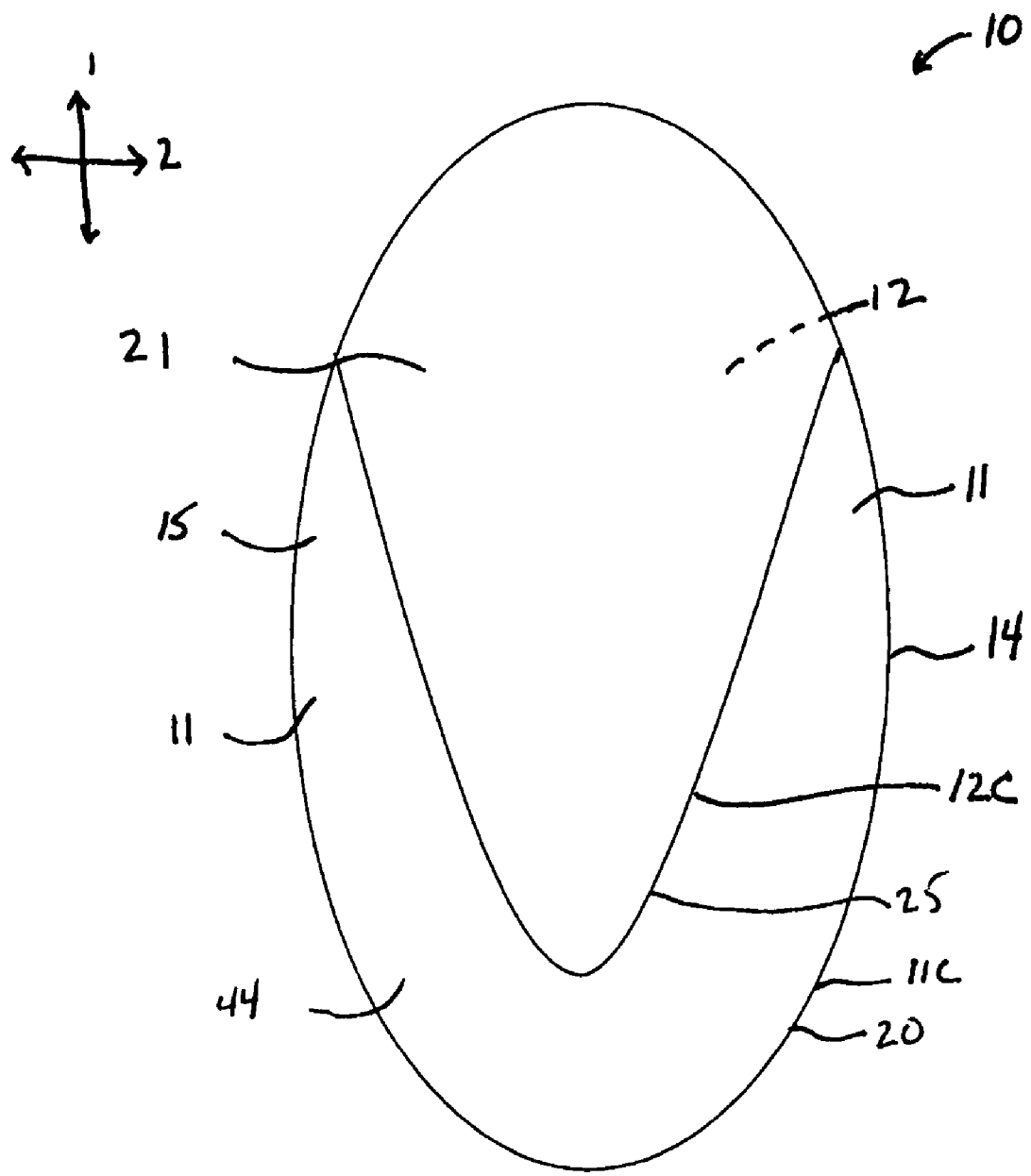
FIGS. 1A and 1B each show a top view of an embodiment of an absorbent article of the present invention.

It should be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

It should be understood that the term "absorbent product" or "absorbent article", as used herein, refers to any article used to control bodily fluids that are configured to absorb and retain bodily exudates, including urine, blood, menses, and other bodily discharges, such as sweat and vaginal secretions resulting from sexual activity and the like.

As used herein, the term "polymer" generally includes, but is not limited to, homopolymers, copolymers, such as for example, block, graft, random and alternating copolymers, terpolymers, etc., and blends and modifications thereof. Furthermore, unless otherwise specifically limited, the term "polymer" shall include all possible geometrical configurations of the material. These configurations include, but are not limited to, isotactic, syndiotactic and random symmetries.

As used herein, "body-facing surface" means that surface of the absorbent article which is intended to be disposed toward or placed adjacent to the body of the wearer during ordinary use. The "garment-facing surface" is on the opposite side of the absorbent article from the body-facing surface. The garment-facing surface is an outward surface of the absorbent article and is intended to be disposed to face away from the wearer's body during ordinary use. The garment-facing surface is generally arranged to face toward or placed adjacent to the wearer's undergarments when the absorbent article is worn.

As used herein, the term "connected" is intended to mean directly connected and indirectly connected. By directly connected, it is intended that the connected elements are in contact with one another or affixed to one another. By indirectly connected, it is intended that one or more intervening or intermediate elements are between the two elements which are secured or "connected" together. The intervening elements may be affixed.

As used herein, the term "absorbent structure" is intended to mean a configuration of an absorbent material which allows fluids to be absorbed by the absorbent material.

DETAILED DESCRIPTION OF THE INVENTION

The absorbent product of the present invention provides an absorbent article which is designed to adhere to the body of a user in the area of the body of the user which may need bodily fluids absorbed. In one particular use of the absorbent article, the absorbent article is attached to the body of a female user to or around the vulva region of the body. By "to or around the vulva region", it is meant adjacent regions of the body of a female including the pubic region and the perinea region. When applied to or around the vulva region of the female body, the absorbent article may be used as a pantiliner, sanitary napkin or incontinence article. In addition, the absorbent article may be worn as an underwear substitute since the absorbent article of the present invention does not need underwear hold the absorbent article in place. As an underwear substitute, the absorbent article provides protection to the vulva area by creating a barrier between the outer clothing and the vulva of a user. When worn as an underwear substitute, the absorbent article serves to protect the outer clothing of the wearer from bodily discharges from the vulva region of the user's body. In addition, when the absorbent article is worn as an underwear substitute, the absorbent article also serves to protect the sensitive skin and body features of the vulva region from roughness of the outer clothing, there by preventing or alleviating irritation to the sensitive skin and body features of the vulva region.

Figure 2:
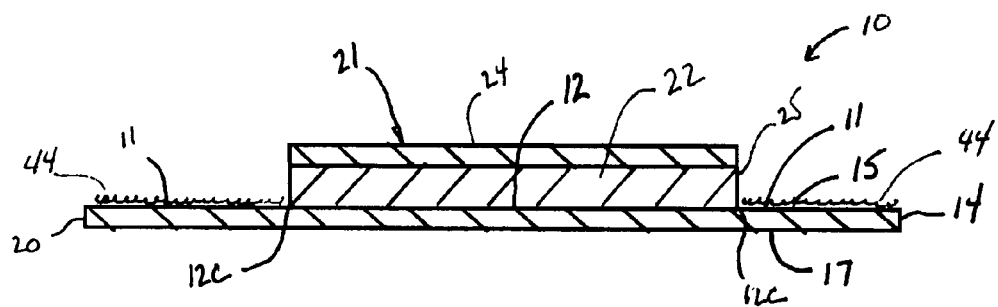
FIG. 2 shows a side cross-sectional view of an embodiment of an absorbent article of the present invention.
Figure 4:
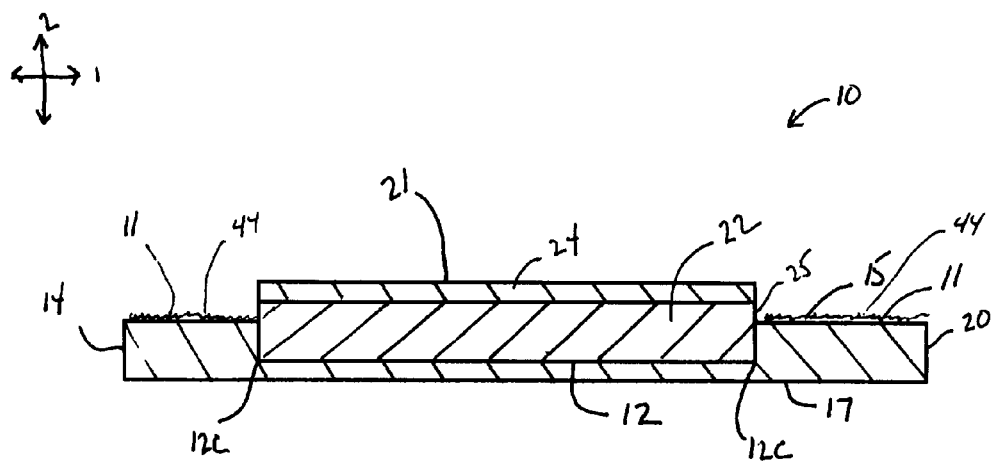
FIG. 4 shows a cross-sectional side view of an absorbent article of the present invention with the absorbent core recessed into the shell.

To gain a better understanding of the present invention, attention is directed to the Figures of the present specification. As is shown in each of the Figures, the absorbent article 10 has a longitudinal direction 1 and a lateral direction 2. One component of the absorbent article is a shell 14. This shell 14 has a first side 15 and a second side 17, as is shown in FIGS. 2 and 4. The shell 14 serves to provide the overall contour or silhouette of the absorbent article of the present invention. In addition, the shell 14 also provides a surface for attachment or adhesion of the absorbent article 10 to the body of a user.

Figure 1B:
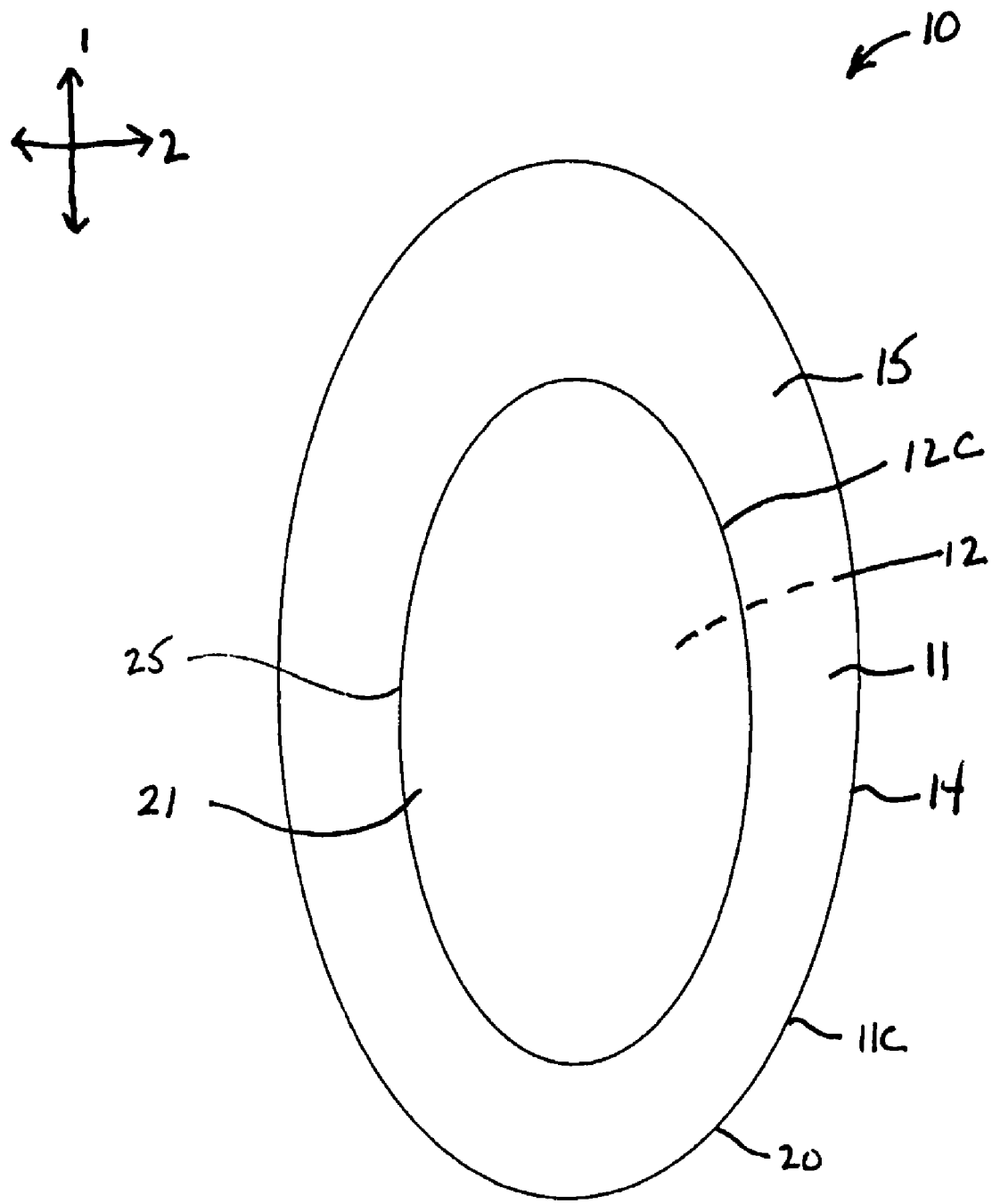

The first side 15 of the shell 14 is the body facing side of the absorbent article 10 and the second side 17 of the shell 14 is the garment facing side of the absorbent article. The first side 15 of the shell 14 has a first area 11 and a second area 12. The first area 11 surrounds or bounds the majority of the second area 12, as is clearly shown in FIG. 1A. By "surrounds or bounds the majority", it is meant that at least 51% of the circumference 12C of the second area 12 contacts the first area 11. Generally, at least 60% of the circumference 12C of the second area 12 contacts the first area 11. In a particular embodiment, at least 75% of the circumference 12C of the second area 12 is in contact with the first area 11. In another particular embodiment, at least 90% of the circumference 12C of the second area 12 is in contact with the first area 11. In a further embodiment of the present invention, at least 95% of the circumference 12C of the second area 12 is in contact with the first area 11. In a further embodiment of the present invention, the first area 11 completely surrounds the second area 12 of the shell 14 as is shown in FIG. 1B.

In one embodiment, the first area 11 of the first side of the shell 14 is designed or adapted to contact, attach or adhere to the wearer's skin. In one particular embodiment, the first area 11 of the shell 14 is designed or adapted to contact a female wearer's skin surrounding the vulva region of the female torso when the absorbent article 10 is applied to the wearer. By "designed or adapted to contact a female wearer's skin surrounding the vulva region of the female torso", it is meant that the size and shape of the shell is such that the shell fits in the vulva region and possibly the surrounding pubic region and perinea regions of the female torso. Generally, the shell 14 is sized and shaped such that the extent of the first area of the shell only contacts and attaches or adheres to the skin surrounding and proximate to the vulva area and possibly the pubic and perinea regions of the wearer. In addition to contacting the skin in the vulva, pubic and perinea regions of the wearer, the first area 11 of the first area of the shell 14 may also contact and attach or adhere to any hair in the vulva area of the user which may be present. The first area 11 is the portion of the first side 15 of the shell 14 which holds the absorbent article in place on the user.

Generally, the second area 12 of the shell 14 is the portion of the shell 14 which provides absorbency to the absorbent product. That is, the second area 12 of the first side to the shell is any area of the first side of the shell which has an absorbent structure attached thereto, or has absorbent properties. In one particular embodiment of the present invention, the second area 12 of the shell 14 has an absorbent structure 21 contained therein or attached to the shell 14 in the second area. It is noted that the second area 12 may be a single contiguous area or may be two or more distinct areas. Generally, the second area 12 is a single contiguous area from an ease of manufacturing standpoint. In an alternative embodiment, the second area 12 of the shell may contain an absorbent material integrated into the shell 14, such that the second area 12 of the shell is absorbent without the presence of an additional absorbent structure. The second area 12 shell may have an absorbent material coated or impregnated into the shell material.

To gain a better understanding of the vulva region and surround regions of the female body, a general description of the anatomical structures can be found in *The Illustrated Running Press Edition of the American Classic Gray's Anatomy* (1974) by Henry Gray and *Structure and Function in Man* (1974) by Stanley W. Jacob, M.D., F.A.C.S. and relevant portions are included herein by reference. The general form can be found in *Anatomy for an Artist: Elements of Form* by Eliot Goldfinger and relevant portions are included herein by reference. The general description of the pubic hair covering these regions can be found in *Woman's Body: A Manual for Life* and relevant portions are included herein by reference.

The female anatomical structures to be described include the leg and the lower torso. The external anatomical structures of the lower torso include gluteal region and perineum region. The gluteal region includes the buttocks and the anus. The anatomical structure involved on the leg is the medial surface of the upper thigh.

The gluteal region includes generally the buttocks and anus and is typically bound in front by the line of the buttocks and the gluteal folds, in the back by the sacral triangle and the sides by lines extending through the greater trochanters. The shape of the gluteal region is roughly hemi-spherical and convex, and is determined by a series of muscles including the gluteus maximus and a series of fat pads including the posterior gluteal fat pad. The line of the buttocks separates the gluteal region and the perineum region.

The upper thigh region includes typically the right and left thigh and is typically bound on top by the thigh lines and the sides by the front and back of the leg. The thigh lines are two lines that are on either side of the labia and each of the lines runs along the line of the inguinal ligament to the gluteal folds and marks where the upper thigh meets the lower torso. The shape of the region is roughly a portion of a tapered cylinder and convex, and is shaped by a series of muscle groups including the gracilis, pectineus, adductor longus, adductor brevis, and adductor magnus and series of fat pads including the inner thigh fat pad.

The perineum region, which extends from the inferior outlet of the pelvis to the bony structure of the coccyx, is comprised of two divisions, the urogenital triangle and the anal division or obstetrical perineum. The region includes the external organs of reproduction; the mons pubis, labia majora and minora, clitoris, meatus urinarius and the opening to the vagina. The region is generally bound in front by the lower abdominal line, on the sides the thigh lines, and in the back the line of the buttocks. The abdominal line is a line that passes across the top of the pubis. The lines of the buttocks are lines that connect the thigh lines to the gluteal cleft. For convenience in describing the form and created spaces in the perineum region, this region will be subdivided into three regions including an anterior region including the mons pubis, a central region including the labia majora and minora, and posterior region. The anterior region is bound in front by the lower abdominal line, in back by anterior commissure, and on the sides by line of the labia. The central region is bound in front by the anterior commissure, in the back by the posterior commissure, and on the side by the line of the labia. The posterior region is bound in front by the line of the labia, in the back by the lines of the buttocks, and on the sides the thigh line.

The vulva region includes the female external genitalia and generally includes the anterior and central regions of the perineum. The mons pubis [or veneris] is generally a rounded eminence in front of the symphysis pubis, formed by a collection of fatty tissue including the pubic fat pad beneath the integument and is generally covered with pubic hair. The labia majora are generally two prominent longitudinal cutaneous folds extending downward from the mons veneris to the anterior boundary of the perineum, and generally enclosing the common urinary-sexual opening. The space between the two folds is the labial cleft. Each labium has generally two surfaces, an outer, which is pigmented and covered generally with strong, crisp pubic hairs, and an inner within the labia cleft, which is smooth and is beset with large sebaceous follicles and is continuous with the genito-urinary mucous tract; between the two there is considerable quantity of areolar tissue, fat including the labia fat pad, and tissue besides vessels, meeting the anterior commissure. Posteriorly they are typically not joined, but generally appear to become lost in the neighboring integument, terminating close to, and nearly parallel with each other. Together with the connecting skin between them, they form the posterior commissure or posterior boundary of the vulval orifice. The interval between the posterior commissure and the anus constitutes the perineum region. The fourchette is the anterior edge of the perineum, and between it and the hymen is a depression, the fossa navicularis. The line of the labia separates the labia and the perineum region.

The labia minora are two small cutaneous folds, situated generally within the labia majora, and extending from the clitoris obliquely downward, outward, and backward on each side of the orifice of the vagina, between which and the labia majora they are lost.

The form of the perineum, gluteal, and upper thigh regions combine to form a very intricate skin topography and spaces. The roughly two-hemispherical-like forms of the buttocks, the roughly tapered-cylinder-like form of the upper thigh, split-teardrop-like form of the vulvar region create intricate generally convex topography with intersections to form a series of recesses. The generally convex topography of the buttocks, the vulvar region, and upper thigh join to create spaces including two inner thigh grooves along two thigh lines, a depression in the posterior perineum region and a cleft extending through the labia and gluteal clefts. The grooves, depression, and cleft are like interconnected recesses in the topography. The central region general has lateral sides separated by a distal surface created by the labial cleft and includes the labial cleft.

Pubic hair generally cover some of these regions and fill in a portion of these recesses especially the labial cleft and the portion of the groove of the thigh parallel to the labial cleft to create a hair surface topography. The hair topography is the surface topography of an imaginary distal surface created by the hair. The depression of the perineum, thigh groove parallel to the gluteal cleft, and the gluteal cleft generally has little or no pubic hair. The skin topography combines with the hair topography to create an overall body topography.

This intricate space created by the intricate body form in this region of the body varies between women in both size and form, and varies with the position and movement of the women. Some of these variations are summarized in "Female genital appearance: 'normality' unfolds" by Jillian Lloyd et. al., *BJOG: An International Journal of Obstetrics and Gynecology*, May 2005, Vol. 112, pp. 643-646 and is included herein by reference.

Figure 2A:
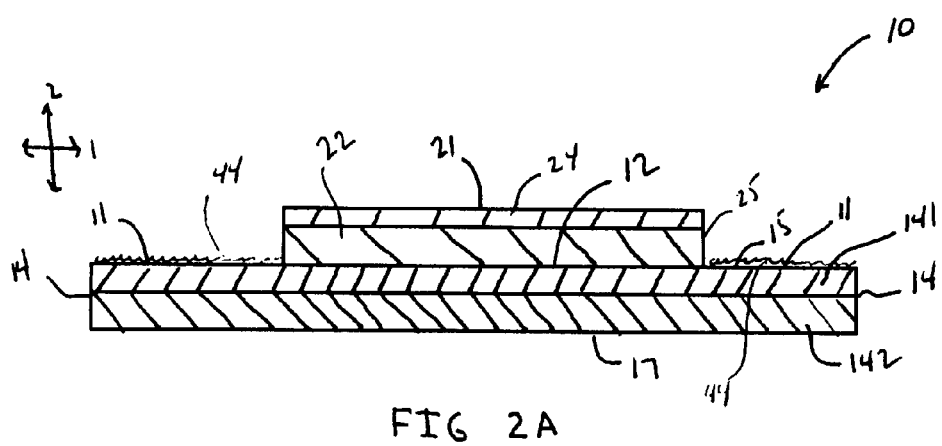

The shell 14 of the absorbent article 10 may be prepared from a variety of materials. The shell may include a layer constructed of any material which will function to be operatively liquid impermeable. The shell 14 may, for example, include a polymeric film, a woven fabric, a nonwoven fabric or the like, as well as combinations or composites thereof. For example, the shell 14 may include a polymer film laminated to a woven or nonwoven fabric. A laminate shell 14 structure is shown in FIG. 2A, having an upper layer 141 and a lower layer 142, wherein the upper layer is the body-facing side of the shell 14 and the lower layer 142 is the garment facing side of the shell 14. In a particular feature, the polymer film can be composed of polyethylene, polypropylene, polyester, silicone or the like, as well as combinations thereof. Additionally, the polymer film may be micro-embossed, have a printed design, have a printed message to the consumer, and/or may be at least partially colored. Suitably, the shell 14 can operatively permit a sufficient passage of air and moisture vapor out of the absorbent article 10, particularly out of an absorbent structure 21 while blocking the passage of bodily fluids and odors often associated with bodily fluids. An example of a suitable shell material can include a breathable, microporous film, such as those described in, for example, U.S. Pat. No. 6,045,900 to Haffner et al., the entire disclosure of which is incorporated herein by reference and made a part hereof. Other shell materials which are extensible may be used in the present invention. Examples of extensible backsheet materials are described in U.S. Pat. No. 5,611,790, issued Mar. 18, 1997, to Osborn, III et al., herein incorporated by reference in its entirety.

In one particular embodiment of the present invention, the shell 14 may be a laminate of a woven or nonwoven fabric with a silicone polymer, wherein the silicone polymer has adhesive properties. The second side 17 of the shell will be woven or nonwoven fabric and the first side 15 of the shell will be silicone polymer. One commercially available laminate is an Oleeva Fabric® I available from Bio Med Sciences, Inc., which have offices at 7584 Morris Court, Suite 218 Allentown, Pa. 18106. The Oleeva Fabric® is a silicone sheeting having adhesive properties laminated to a fabric backing. The silicone sheeting will form the body facing first side 15 of the shell material. Relating this particular structure to the Figures, in FIG. 2A, the silicone polymer is the upper layer 141 of the shell 14 and the nonwoven or woven layer is the lower layer 142 of the shell.

Bicomponent films or other multi-component films can also be used as the shell 14 material. In addition, woven and/or nonwoven fabrics which have been treated to render them operatively liquid-impermeable can also be used as an effective shell 14 material. Another suitable shell material can include a closed-cell polyolefin foam, a polyurethane polymer material, a silicone polymer or other similar materials. Silicone polymers having naturally occurring adhesive properties, or silicone polymers having a silicone adhesive layer applied thereto are of particular interest for the shell material. Such silicone polymers will allow the first area 11 of the shell 14 to adhere to the body of the user without the need of an additional adhesive. These materials may be laminated to another material such that the second side 17 of the shell 14, which is the garment facing side of the absorbent article 10, so that the adhesive nature of the silicone polymer does not adhere the garment of under garments of the user. In another embodiment of the present invention, the shell material may be prepared from an interpenetrating polymer network or two or more polymers. Generally, one of the polymer of the interpenetrating polymer network may be a silicone material. Examples of interpenetrating polymer networks are described in U.S. Pat. No. 5,759,560, issued to Dillion, which is hereby incorporated by reference in its entirety.

The shell material should be selected such that the overall properties of the shell allow the shell material to move the skin of the user during normal use and normal movements by the user during use. By "normal movement by the user" it is meant any movement that normally occurs during use of the absorbent article, including, walking, running, sitting, standing, kneeling, riding a bicycle, exercising, playing sports, getting into and out of an automobile, and other similar movements made by users when wearing an absorbent article. The shell should not be too rigid, such that the shell detaches from the skin of the user during use and the shell should not be so flexible that the shell tends to twist and bunch during use. The shell should have sufficient flexibility to conform to the skin of the user and become similar to a second skin of the user.

Generally, the shell material should have sufficient thickness to allow the shell 14 to mold to the body of the user, but not too thick that the shell 14 becomes uncomfortable for the user to wear. In addition, the shell 14 should not be so thin that it ineffectively forms a seal with the skin of the user when applied to the user, or becomes detached from the skin of the user during use and normal movement of the user during use or that it does not adequately conform to the shape and skin of the user at the point of attachment to the user. Depending on the material used for the shell, the typical thickness of the shell is between 0.03 mm and about 5.0 mm, more particularly between 0.1 mm and 3.0 mm. In one particular embodiment, the thickness of the shell is between 0.25 mm and about 3.0 mm. Again, the actual thickness used is dependent of several factors including rigidity of the material, the flexibility of the material and the ability of the material to assume the shape of the skin of the user at the location of use, which is typically the vulva region of a user.

The second side 17 of the shell 14 forms the garment-facing side of the absorbent article when worn by a user. The shell material should be selected such that the second side of the shell will freely move against the undergarment or clothing of a user. One way to achieve this result is to have the second side 17 of the shell 14 to have a fairly low coefficient of friction. This will allow the second side 17 of the shell 14 to freely move against the undergarment or other clothing worn by the user. If the second side 17 of the shell 14 does not freely move against the undergarment or other clothing worn by the user, the absorbent article may catch on the undergarment or clothing, which may result in the absorbent article being prematurely and undesirably removed from the user or may cause the absorbent article to be shifted from its desired placement against the body of a user.

In order to achieve the desired coefficient of friction on the second side 17 of the shell 14, the materials used to prepare the shell could be selected such that the second side 17 of the shell material will inherently have the desired coefficient of friction. Alternatively, the second side 17 of the shell 14 may be treated with a coating composition, such a polytetrafluoroethylene containing coating, a silicone containing coating or other similar coating having low coefficient of friction properties. Alternatively, the shell 14 could be made from a laminate of two or more materials such that the first side 15 of the shell 14 is prepared from a material which meets the needed properties of the first side 15, while the material selected for the second side 17 of the shell 14 meets the desired coefficient of friction such that the second side 17 will free move against the undergarment or garment being worn by a user.

Figure 3:
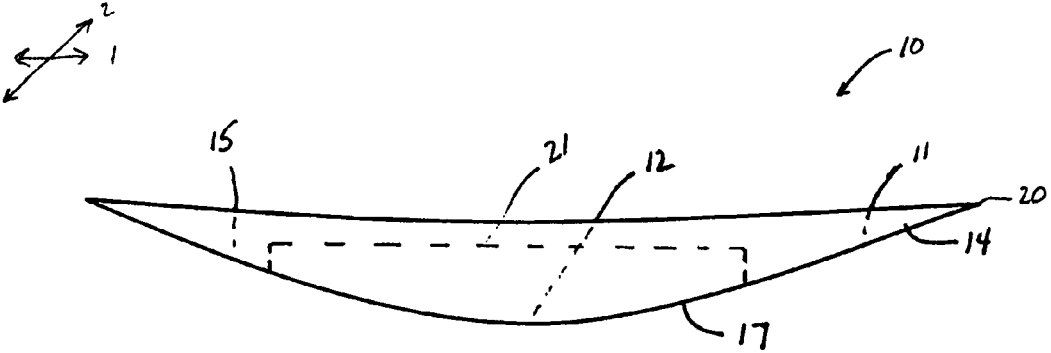
FIG. 3 shows a side view of another embodiment of an absorbent article of the present invention wherein the shell has a concave shape.

The shell 14 of the absorbent article 10 may be flat or may have a three-dimensional shape. As is shown in FIG. 3, which is a side perspective view of the absorbent article the shell 14 has a three-dimensional concave shape. Alternatively, as is shown in cross-sectional side views of FIGS. 2, 2A and 4, the shell 14 may have a generally flat shape. By providing the absorbent article 10 with a three-dimensional concave shape as is shown in FIG. 3, placement of the article may be easier for the user. Generally, the three-dimensional shape could be such that it closely matches the overall general curvature of the vulva region and optionally the pubic and perinea regions of most women, when the absorbent article is used as a pantiliner, sanitary napkin or a feminine incontinence article. To form the shell 14 with a three-dimensional shape, the shell may be molded in any manner known to those skilled in the art, for example heat molding. The manner in which the three-dimensional shape is imparted to the shell 14 is not critical to the present invention.

Figure 5:
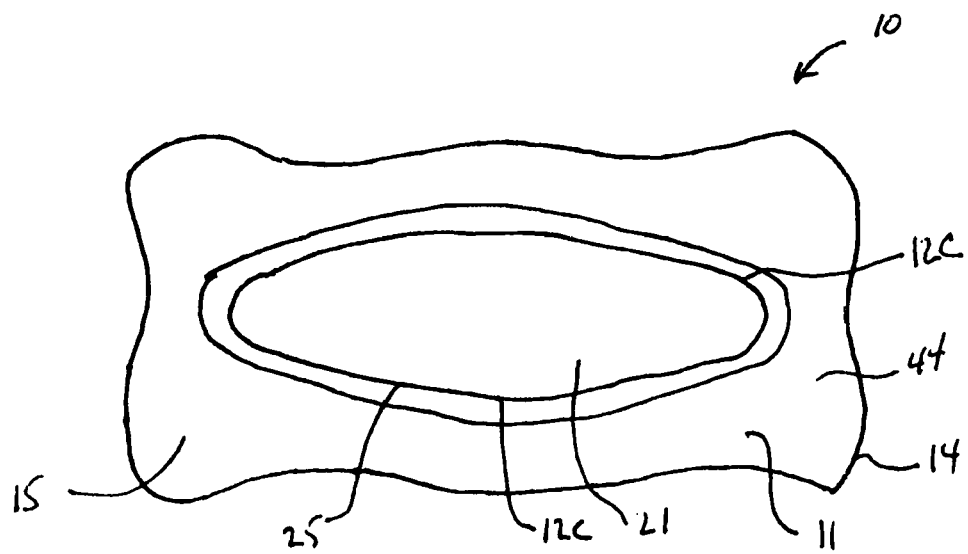
FIGS. 5, 5A and 5B each show a top view of an embodiment of an absorbent article of the present invention having a different shell shape.
Figure 5A:
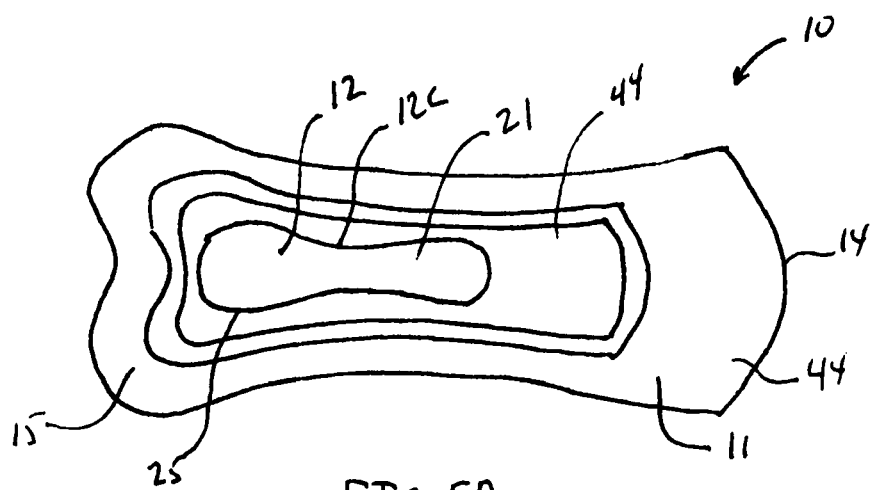
Figure 5B:
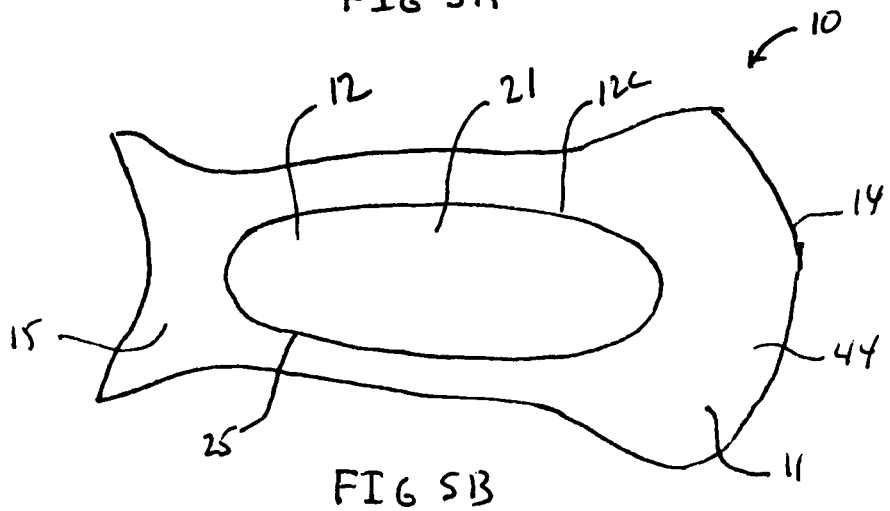

When the shell 14 is a flat shape, meaning that the shell does not have a third dimension other than thickness, the shell 14 should be made to be flexible enough that the shell 14 can conform to the body of the user at the point of attachment. In addition to being flat, the overall shape of the shell 14 may be contoured, as is shown in FIGS. 5, 5A and 5B. In one embodiment, the contour shape may be such that the narrowest point of the contour is in the crotch area of the shell 14 nearest the vulva region, as is shown in FIG. 5A. The contour shape shown in FIG. 5 is one of many possible shapes the shell 14 and absorbent article may be prepared. Other shapes may be used, without departing from the scope of the present invention. Generally, the shape selected should be such that the shell 14 and absorbent article 10 are comfortable for the user to wear, while providing leakage protection to the user. It is noted that a contour shape may also be used in conjunction with a three-dimensional shell. Further discussion of the overall shape of the absorbent article may be found below.

The shell may be any desired color or may be translucent. In addition, the shell may have a matt finish, satin finish or a smooth finish. The particular finish color or translucency can be a matter of choice for the manufacturer of the absorbent article of the present invention. However, by providing a shell which is translucent may assist the user in placing the absorbent article 10 prior to use, since the user may be able to see where the article is placed compared to the genitalia of the user.

The absorbent structure 21 is designed to absorb body exudates, including menstrual fluid, blood, urine, and other bodily fluids, such as sweat and vaginal discharges. The absorbent structure 21 has a longitudinal direction 1 and a lateral direction 2. This absorbent structure 21 may be a single layer or may be multiple layers. Typically, the absorbent structure 21 has an absorbent core 22. This absorbent core 22 may contain one or more layers of absorbent materials. That is the absorbent core 22 may be a single layer of absorbent materials or may be a multilayer structure. Each of the layers can contain similar materials or different materials. In the absorbent article 10 of the present invention, the materials which may be used to form the absorbent core 22 include those materials conventionally used in absorbent articles and includes materials, such as, for example, cellulose, wood pulp fluff, rayon, cotton, and meltblown polymers such as polyester, polypropylene or coform. Coform is a meltblown airformed combination of meltblown polymers, such as polypropylene, and absorbent staple fibers, such as cellulose. A desired material is wood pulp fluff, for it is low in cost, relatively easy to form, and has good absorbency.

The absorbent core 22 can also be formed from a composite comprised of a hydrophilic material which may be formed from various natural or synthetic fibers, wood pulp fibers, regenerated cellulose or cotton fibers, or a blend of pulp and other fibers. One particular example of a material which may be used as the absorbent core is an airlaid material. The absorbent core 22 may have other properties including extensibility, which will allow the absorbent core to be extended or fit to a particular user. One example of extensible absorbent cores is described in U.S. Pat. No. 5,611,790, issued Mar. 18, 1997, to Osborn, III et al., herein incorporated by reference in its entirety.

In one embodiment, the absorbent core 22 may also include a superabsorbent material, in addition to or in place of the hydrophilic material, which increases the ability of the absorbent core to absorb a large amount of fluid in relation to its own weight. Generally stated, the superabsorbent material can be a water-swellable, generally water-insoluble, hydrogel-forming polymeric absorbent material, which is capable of absorbing at least about 15, suitably about 30, and possibly about 60 times or more its weight in physiological saline (e.g. saline with 0.9 wt % NaCl). The superabsorbent materials can be inserted as particles or in sheet form. The superabsorbent material may be biodegradable or bipolar. The hydrogel-forming polymeric absorbent material may be formed from organic hydrogel-forming polymeric material, which may include natural material such as agar, pectin, and guar gum; modified natural materials such as carboxymethyl cellulose, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridine, and the like. Other suitable hydrogel-forming polymers include hydrolyzed acrylonitrile grafted starch, acrylic acid grafted starch, and isobutylene maleic anhydride copolymers and mixtures thereof. The hydrogel-forming polymers may be lightly crosslinked to render the material substantially water insoluble. Crosslinking may, for example, be by irradiation or covalent, ionic, Van der Waals, or hydrogen bonding. Hydroxyfunctional polymers have been found to be good superabsorbents for sanitary napkins. Such superabsorbents are commercially available from Dow Chemical, Hoechst-Celanese, and Stockhausen, Incorporated, among others, and are a partially neutralized salt of cross-linked copolymer of polyacrylic acid and polyvinyl alcohol having an absorbency under load value above 25 grams of absorbed liquid per gram of absorbent material (g/g). Other types of superabsorbent materials known to those skilled in the art can also be used.

Generally, the absorbent core 22 will be positioned adjacent the shell 14, as is shown in FIGS. 2, 2A and 4. In addition, the absorbent core 22 may be recessed into the shell 14 as is shown in FIG. 4. By "adjacent to the shell", it is meant that the that the absorbent core 21 is directly in contact with the shell or may be separated by one or two additional layers or a construction or pressure sensitive adhesive.

In addition to the absorbent core 22, the absorbent structure 21 may have other additional layers which aid the absorbent core 22 in capturing and holding the bodily fluid into the absorbent core 22. These other layers, when present, in combination with the absorbent core 22 form the absorbent structure 21 of the absorbent article 10. There may be a single layer or multiple layers in addition to the absorbent core in the absorbent structure 21. Alternatively, the absorbent structure 21 may have a single layer, which is generally the absorbent core 22.

One particular example of an additional layer which may be used in addition to the absorbent core 22 in the absorbent structure 21 is a body-side liner or top sheet 24, which is generally a liquid permeable material, which allows bodily fluids to pass through the top-sheet into the absorbent core. It is noted that the terms "body-side liner" and "top sheet" may be used interchangeable. The body side liner 24 also may provide a user with a dry feeling by separating the absorbent core 22 from the body of the user. That is, the body-side liner 24 is placed between the absorbent core 22 and the body of the user and such that the absorbent core 22 is between the body side liner 24 and the shell 14.

In the present invention, generally the body side liner 24 will only extend to the edge 25 of the absorbent core, as is shown in FIG. 2. However, the body side liner 24 may extend beyond the edge 25 of the absorbent core 22 and may be attached to the first side of the shell. Generally, if the body side liner 24 extends beyond the absorbent core 22, the body side liner will be attached to the first side 15 of the shell 14. Also, if the body side liner 24 extends beyond the absorbent core 22, the body side liner 24 will generally not cover the entire first area 11 of the first side 15 of the shell 14.

Optionally, the body side liner 24 may be formed from one or more materials. The body-side liner or top sheet 24 should be able to manage different body excretions depending on the type of product. In feminine care products, often the body-side liner or top sheet 24 must be able to handle menses and urine. In the present invention, the body-side liner or top sheet 24 may include a layer constructed of any operative material, and may be a composite material. For example, the body-side liner or body-contacting layer can include a woven fabric, a nonwoven fabric, a polymer film, a film-nonwoven fabric laminate or the like, as well as combinations thereof. Examples of a nonwoven fabric useable in the body-side liner or top sheet 24 include, for example, an airlaid nonwoven web, a spunbond nonwoven web, a meltblown nonwoven web, a bonded-carded web, a hydroentangled nonwoven web, a spunlace web or the like, as well as combinations thereof. Other examples of suitable materials for constructing the body-side liner or top sheet 24 can include rayon, bonded-carded webs of polyester, polypropylene, polyethylene, nylon, or other heat-bondable fibers, finely perforated film webs, net-like materials, and the like, as well as combinations thereof. These webs can be prepared from polymeric materials such as, for example, polyolefins, such as polypropylene and polyethylene and copolymers thereof, polyesters in general including aliphatic esters such as polylactic acid, nylon or any other heat-bondable materials. When the body-side liner is a film or a film laminate, the film should be apertured or otherwise be made to allow fluids to flow through the body-side liner to the absorbent core.

Other examples of suitable materials for the body-side liner or top sheet 24 are composite materials of a polymer and a nonwoven fabric material. The composite materials are typically in the form of integral sheets generally formed by the extrusion of a polymer onto a nonwoven web, such as a spunbond material. In a particular arrangement, the body-side liner or top sheet layer 24 can be configured to be operatively liquid-permeable with regard to the liquids that the article is intended to absorb or otherwise handle. The operative liquid-permeability may, for example, be provided by a plurality of pores, perforations, apertures or other openings, as well as combinations thereof, which are present or formed in the liner or body contacting layer. The apertures or other openings can help increase the rate at which bodily liquids can move through the thickness of the liner or body contacting layer and penetrate into the other components of the article (e.g. into the absorbent core 22). The selected arrangement of liquid permeability is desirably present at least on an operative portion of the body-side liner or top sheet 24 that is appointed for placement on the body-side of the article. The body-side liner or top sheet 24 can provide comfort and conformability, and can function to direct bodily exudates away from the body and toward the absorbent core 22. The body-side liner or top sheet 24 can be configured to retain little or no liquid in its structure, and can be configured to provide a relatively comfortable and non-irritating surface next to the body tissues of a wearer. In the present invention, the top sheet or body-facing surface of each absorbent article may be embossed, printed or otherwise imparted with a pattern.

Additional layers or substrates, including for example, the liquid acquisition and distribution layer, also referred to as a surge or transfer layer, and an optional tissue layer are also incorporated into the absorbent structure 21 of the absorbent product 10, for example, between the body-side liner or top sheet 24 and the absorbent core 22. The distribution layer may be shorter than the absorbent core or have the same length as the absorbent core 22. The distribution layer serves to temporarily hold an insulting fluid to allow the absorbent core sufficient time to absorb the fluid, especially when a superabsorbent material is present.

In another embodiment, the absorbent core, transfer layer and other components, such as tissue layers, may be free floating (unattached) between the shell 14 and the top sheet 24, and only are secured along only the peripheral edges thereof. Alternatively, the absorbent core 22, transfer layer, if present, and any other layer or component, if present, may be attached to one or both of the shell 14 and top sheet 24 and/or to each other.

The absorbent structure 21, including the absorbent core, is generally attached to the first side 15 of the shell 14 in the second area 12 of the shell. The attachment may be in a permanent manner, meaning that the absorbent structure is generally intended not to be removable by the user of the absorbent article 10. Alternatively, the absorbent structure 21 may be made to be removable by the user, meaning that the absorbent structure 21 may be removed and replaced with another absorbent structure 21 by the user of the absorbent article 10. When the absorbent structure 21 is attached to the shell 14 in a permanent manner, meaning that the absorbent structure is not intended to be removed by the user, a construction adhesive may be used. Examples of useable construction adhesives include any adhesive which will effectively hold the absorbent structure 21 in place, so as not to be separated from the shell 14. Commercially available construction adhesives usable in the present invention include, for example include Rextac adhesives available from Huntsman Polymers of Houston, Tex., as well as adhesives available from Bostik Findley, Inc, of Wauwatosa, Wis. Other means may be used to hold the absorbent structure 21 to the shell including other bonding means, including heat bonding and ultrasonic bonding. When the absorbent structure 21 is removably attached, the absorbent structure 21 is held in place on the shell 14 by a means which will allow the user to remove the absorbent structure. One such means of holding the absorbent structure is by using a pressure sensitive adhesive. Suitable pressure sensitive adhesives include any commercially available pressure sensitive adhesive. Examples of suitable pressure sensitive adhesives usable to removably hold the absorbent structure 21 in place on the shell 14 include pressure sensitive adhesives available from National Starch and, having offices in, Bridgewater, N.J. 08807. By providing an absorbent structure which is removable, the shell may be reused several times without the need to again place the shell when the absorbent needs to be replaced. Also by having a removable absorbent structure, the absorbent structure can be selected by the user prior to use. This would allow the user to select an appropriate level of protection for a given day or allow the user to select a size or shape of the absorbent which the user finds to be more comfortable.

As is stated above, the absorbent structure 21 is located in the second area 12 of the shell 14 and on the first side 15 of the shell member. This size and shape of the absorbent structure may be varied depending of the intended use of the absorbent article and will be discussed in more detail below.

The absorbent structure 21 may a relatively flat structure, as shown in FIGS. 2, 2A, 3 and 4. Alternatively, the absorbent structure may have a three-dimensional shape other that a relatively flat shape. The absorbent structure may have an anatomically correct shape such that the absorbent structure fits within the labia of the user. Anatomically correct shapes of absorbent are generally know to those skilled in the art and are generally found in the interlabial art field. The absorbent structure may be designed to be partially or fully interlabial. Alternatively, a three-dimensional shaped absorbent structure may also be used in the absorbent article 10 which is designed not to fit within the labia majora of the user. That is, the absorbent structure 21 is positioned completely outside the labia during use The size, location and shape of the absorbent structure 21 may also be selected for an intended use. For example, in an overnight use, the absorbent may be located further back on the user towards the perinea region of the user. In an overnight use, the absorbent structure may be larger than in a product intended for daytime use. In a daytime use, the absorbent structure will generally be centrally located of the vulva region.

In an alternative embodiment of the present invention, the absorbent structure 21 is contained within the shell material. That is, the absorbent structure 21 is an integral part of the shell 14 and a separate absorbent structure is not present. One way to achieve an integral absorbent structure is to have a shell which is prepared from a material which is a laminate of two or more materials. The first side 15 of the shell 14 contains an absorbent material within the body facing side of the laminate. For example, superabsorbent particles or materials may be incorporated into the material making up the body facing layer of the laminate. Another way is to place a very light coating onto the first side 12 of the shell material, wherein the coating contains a superabsorbent particles or materials. Of course other absorbent materials, other than superabsorbent materials may be used in place of or in addition to the superabsorbent materials.

Figure 6A:
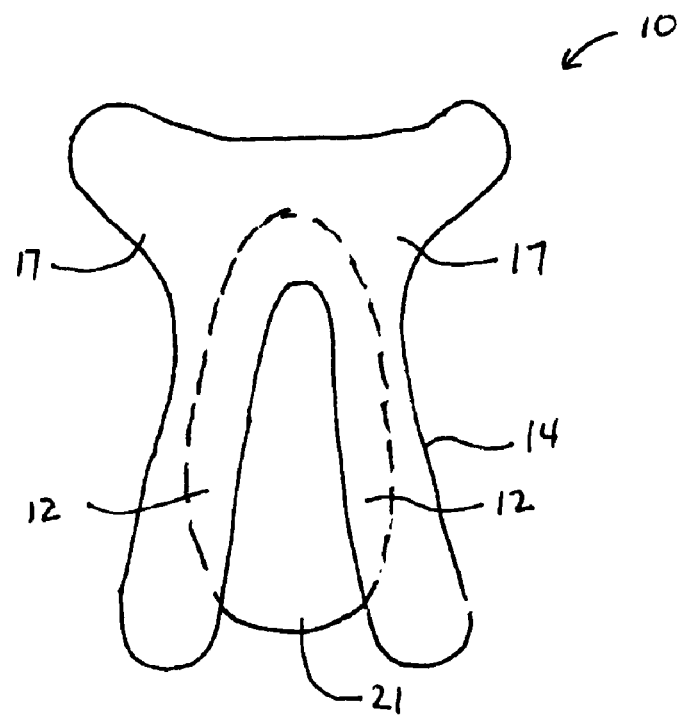
FIG. 6A shows a bottom view of an embodiment of an absorbent article of the present invention where only a portion of the absorbent structure is positioned over shell.
Figure 6B:
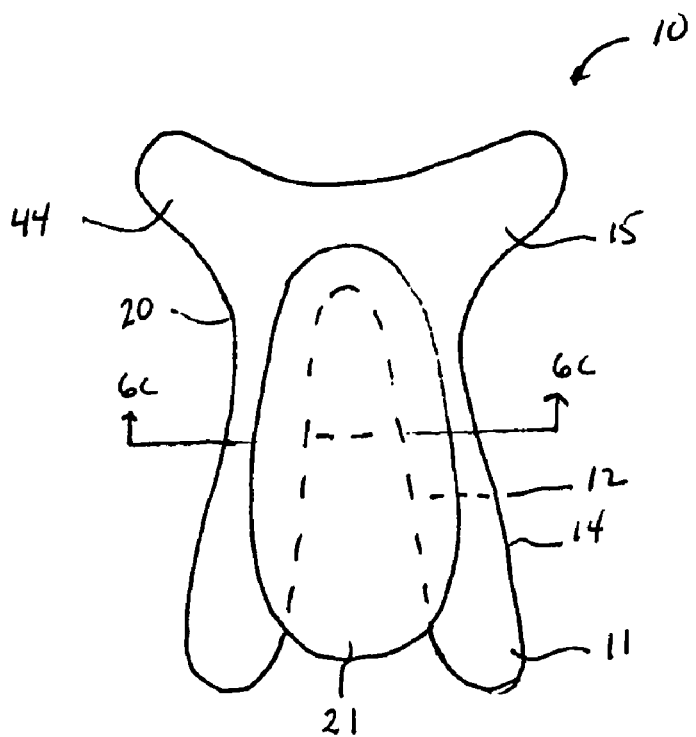
FIG. 6B shows a top view of an embodiment of an absorbent article of the present invention where only a portion of the absorbent structure is positioned over shell.
Figure 6C:
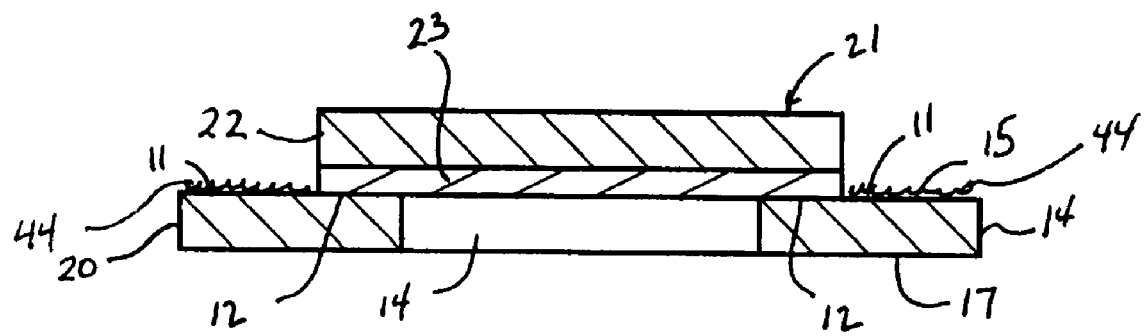
FIG. 6C shows a cross-sectional view taken along sectional line 6C-6C.

The absorbent structure 21 may be located entirely over the shell 14, as is shown in FIGS. 1, 2, 2A, 3, 4 and 5, meaning at the shell 14 material is located beneath the absorbent structure 14. Alternatively, the absorbent structure 21 may be positioned over the shell 14, such that only a portion of the absorbent structure 21 is over the shell 14. This configuration is shown in FIGS. 6A, 6B and 6C. FIG. 6A is a bottom view and FIG. 6B is a top view of an absorbent article 10 within the present invention. As can be seen only a portion of the absorbent structure 21 is positioned over the shell 14. FIG. 6C shows a cross-sectional view of the absorbent article 10 taken along line 6C-6-C in FIG. 6B. As with the other embodiments of the present invention, the portion of the first side 15 of the shell 14 in which the absorbent structure is attached is the second area 12 of the shell 14. Surrounding the second area 12 is the first area 11 of the shell 14. The second side 17 of the shell 14 is the side of the absorbent article which faces the user during use. By having an absorbent article with the structure shown in FIG. 6C, it is also beneficial for the absorbent structure to have an additional layer 23. This additional layer will serve to provide liquid impermeability to the absorbent structure, such that any fluids entering the absorbent core will not flow through the core to clothing of a user.

This additional layer 23 may be prepared from a variety of materials and is generally, this additional layer constructed of any material which will function to be operatively liquid impermeable. The additional layer, may be a polymeric film, a woven fabric, a nonwoven fabric or the like, as well as combinations or composites thereof. For example, the shell 14 may include a polymer film laminated to a woven or nonwoven fabric. In a particular feature, the polymer film can be composed of polyethylene, polypropylene, polyester, silicone or the like, as well as combinations thereof. Additionally, the polymer film may be micro-embossed, have a printed design, have a printed message to the consumer, and/or may be at least partially colored. Suitably, the additional layer can operatively permit a sufficient passage of air and moisture vapor out of the absorbent article 10, particularly out of an absorbent structure 21 while blocking the passage of bodily fluids and odors often associated with bodily fluids. An example of a suitable materials for the additional layer 23 can include a breathable, microporous film, such as those described in, for example, U.S. Pat. No. 6,045,900 to Haffner et al., the entire disclosure of which is incorporated herein by reference and made a part hereof.

As is stated above, the first area 11 of the shell 14 serves either directly or indirectly attaches to the body of a user. Stated another way, the shell is the body attachment member and the first area 11 is the portion of the shell 14 which is attached to the body of the user. Depending on the material selected for the shell, the shell may actively attach to the body of the user using electrostatic means; suction means or a body adhesive may be placed on the first area 11 of the shell 14 to attach the absorbent article to the body of a user. Electrostatic means which can be used is by selecting the shell material to be a material which has an affinity for the body of a user, such that the shell material "clings" to the body of the user. Examples of such materials include ethylene vinyl acetate, low density polyethylene and other similar materials know to those skilled in the art. Suction means may be achieved by shaping the shell to conform to the body of the user, much like a contact lens fits to the eye. Generally, suction means can be achieved by forming the shell 14 into a three-dimensional shape. The easiest way to achieve body attachment is to place a body adhesive in the first area 11 of the shell 14.

The body adhesive 44 is positioned on the first area 11 of the first side 15 of the shell 14. The body adhesive 44 contacts the skin and hair, if present, in the vulva region and possibly the public region and/or the perinea region of the wearer's body, thereby supporting and holding the absorbent article 10 against the body of the wearer during use. The body adhesive 44 can overlie a portion of the first area 11 or can overlie the entire first area 11 of the shell 14. Generally, the body adhesive 44 will be present on a least the outer portion or near the circumference 11C of the first area near the edge 20 of the absorbent article. As is shown in FIGS. 1A, 1B, 2, 2A, 4, 5B and 6B and 6C, the adhesive may cover the entire first area 11 of the absorbent article. Alternatively, the body adhesive 44 may be placed on a portion of the first area 11, as is shown in FIGS. 5 and 5A. The body adhesive 44 may also be placed in a pattern of the first area 11. The body adhesive 44 can be applied to the first area 11 of the shell 14 of using any known process including, inkjet printing, screen printing or extruding the body adhesive 44 from one or more nozzles, slot coating and the like.

Generally, any pressure sensitive adhesive known to those skilled in the art may be used, provided that the pressure sensitive adhesive is not a known irritant to human skin or that the adhesive is so aggressive that it causes pain to the user when the absorbent article is removed from the skin. It is also desirable that the adhesive is selected such that the adhesive does not leave a substantial amount of an adhesive residue on the surface of the skin of the user, when the absorbent article 10 is removed by the user after use. Particularly suitable pressure sensitive adhesive materials are disclosed in the commonly assigned U.S. Pat. No. 6,213,993 to Zacharias et al., U.S. Pat. No. 6,620,143 to Zacharias et al., the entire disclosure of each is incorporated herein by reference and made a part hereof. Other suitable adhesives are disclosed in U.S. Pat. No. 5,618,281 to Batrabet et al., the entire disclosure of which is incorporated herein by reference and made a part hereof. Other known body adhesives, such as those described in U.S. Pat. No. 6,316,524 to Corzani et al. which is hereby incorporated in its entirety, may also be used. Other examples of pressure sensitive adhesives include, Hydrogels, Hydrocolloids, Acrylics based adhesives, rubber based adhesives, such as Kraton based adhesives.

Figure 7:
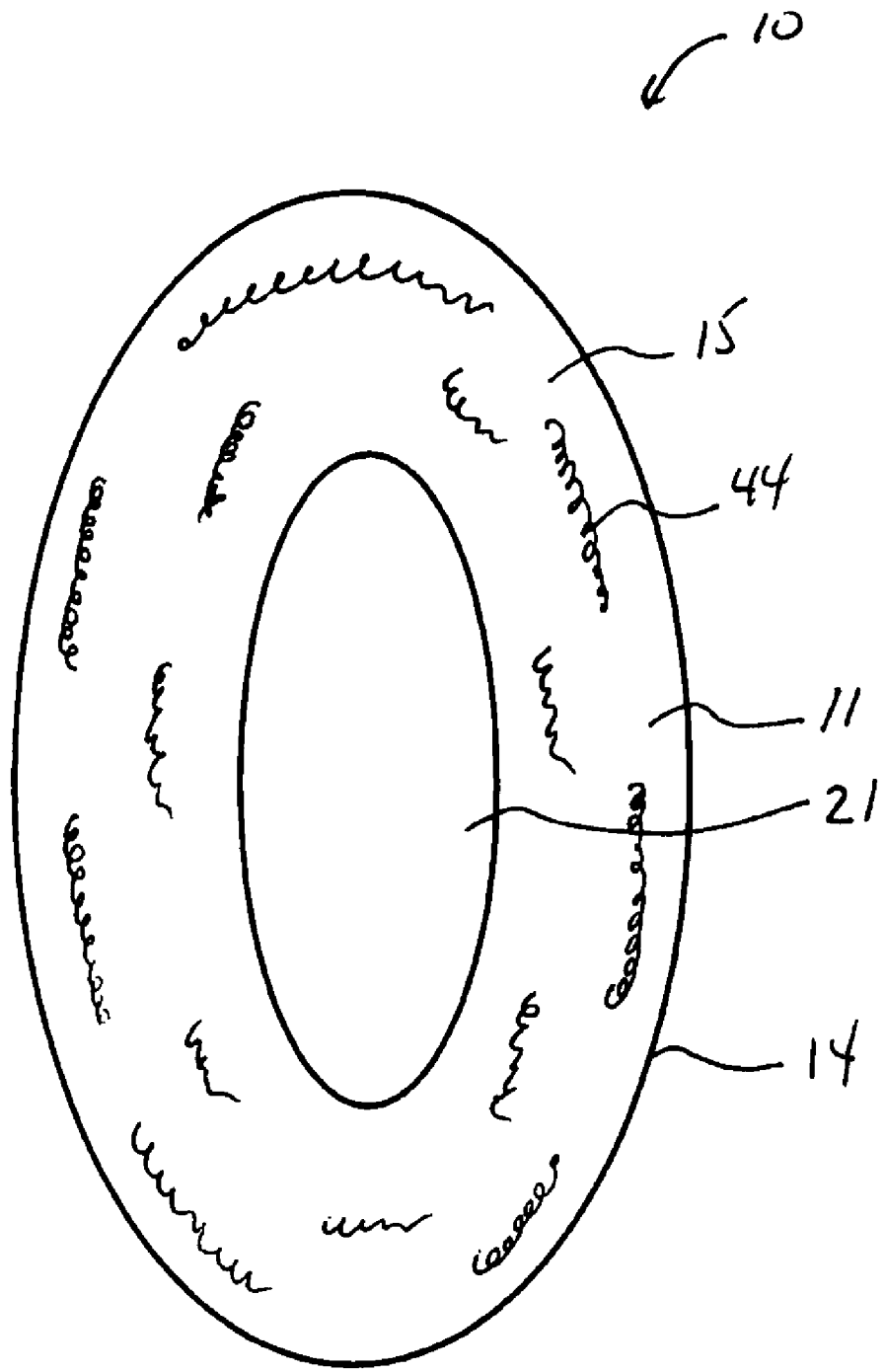
FIG. 7 shows a top view of an embodiment of an absorbent article of the present invention wherein the body adhesive is applied in an open pattern.

The body adhesive 44 may be positioned on the first area 11 of the shell 14 in an open pattern or a closed pattern. By "open pattern" is meant that the adhesive can have an intermittent or discontinuous pattern which does not substantially encircle the entire first area 11. For example, there are breaks in the body adhesive at certain portions of the first area 11. An open pattern of adhesive is shown in FIG. 5. "Closed pattern" means the adhesive 44 would encircle the entire second area 12 of the shell. Preferably, the pattern of the body adhesive 44 will substantially surround the absorbent structure located in or on the second area 12 of the shell 14. As shown in FIGS. 1A, 1B, 2, 2A, 4, 5B and 6B and 6C, the body adhesive 44 is applied in a closed pattern, since the entire body adhesive is applied in a continuous fashion around the first area. An "open" pattern of the adhesive is shown in FIG. 7, which shows the adhesive applied in a discontinuous fashion. Additionally, the adhesive may be applied in portions of the first area 11, as is shown in FIGS. 5 and 5A. In the present invention, the closed pattern can be advantageous since the body adhesive 44 may form a seal with the body of the user which will assist in preventing leaks from the absorbent article 10. The body adhesive may form a dam, which may prevent leaks from the entire perimeter of the absorbent article.

In one embodiment of the present invention, as is shown in FIGS. 1A, 1B, 2, 2A, 4, 5B and 6B and 6C, the body adhesive 44 may be placed on the entire first area 11, just outside of the absorbent structure 21. In another alternative embodiment of the present invention, as is shown in FIG. 5, the body adhesive 44 may placed along the outer portions of the first area 11 near the periphery of the shell 14. The body adhesive 44 may also be placed on the absorbent structure 21. Generally, however, the body adhesive 44 is confined to being placed on the first area 11 of the shell 14, since placing the body adhesive on an area of the absorbent product 10 which contacts the female genitalia such as the labia majora may cause discomfort to the wearer of the absorbent product.

The adhesive may be applied in a pattern of small discrete dots so as to leave numerous areas free from adhesive. Alternatively, the adhesive may be applied as a continuous bead, or may be applied as a series of semi-continuous beads. Other suitable adhesive patterns may be selected for applying the body adhesive 44 to the body-contacting first area 11 of the absorbent article 10. For example, adhesive patterns can be oval, swirls, various linear or non-linear arrays of adhesive longitudinally, and/or transversely oriented and reticulated webs having unobstructed interstices between the adhesive fibers or combinations thereof. As stated above, the adhesive patterns may be open or closed. The weights of adhesives are limited to less than about 800 $g/m^2$, and generally less than about 400 $g/m^2$. Generally, the weight of the adhesive is at least 20 $g/m^2$. Typically, the adhesive is applied in an amount of about 100 to about 400 $g/m^2$. The limitations on the basis weight of the adhesive are important to provide the correct adhesive characteristics for applying directly to the wearer's vulva region and optionally the pubic and perinea regions of the wearer's body. If the basis weight is too high, the absorbent article will have a sticky feeling or otherwise uncomfortable feeling. If the basis weight of the adhesive is too low, there may be insufficient adhesion to the body of the user.

Generally, the body adhesive 44 is applied in a manner which is symmetrical about the longitudinal axis 1 which bisects the absorbent article 10 and divides the absorbent article 10 into substantially equal portions. This symmetrical pattern provides the wearer a balanced feel when wearing the absorbent article 10. The symmetrical pattern also reduces the perception of any associated discomfort when the absorbent article 10 is removed from the body.

Figure 8A:
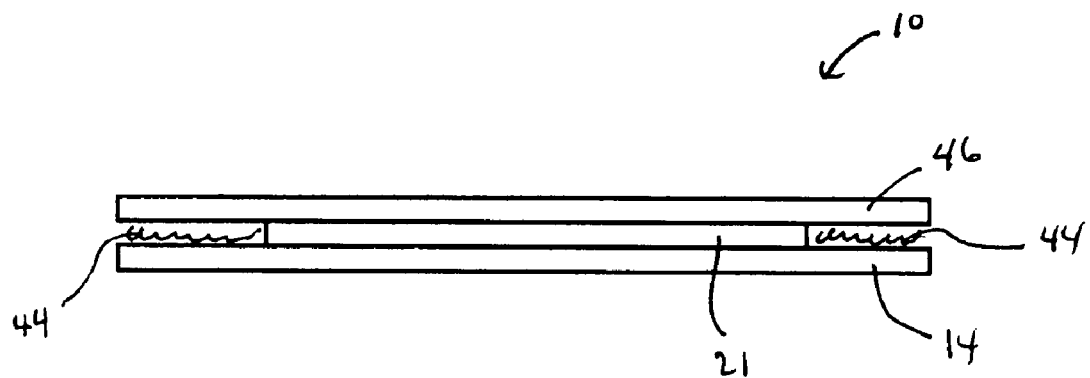
FIGS. 8A, 8B and 8C each show an absorbent article of the present invention having a release sheet applied thereto.
Figure 8B:
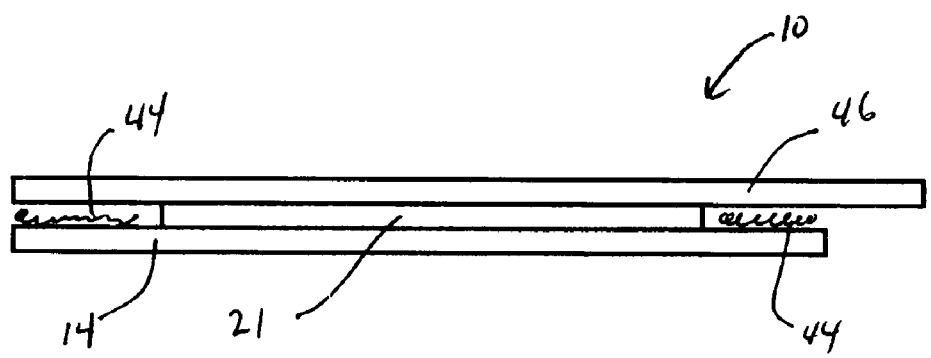
Figure 8C:
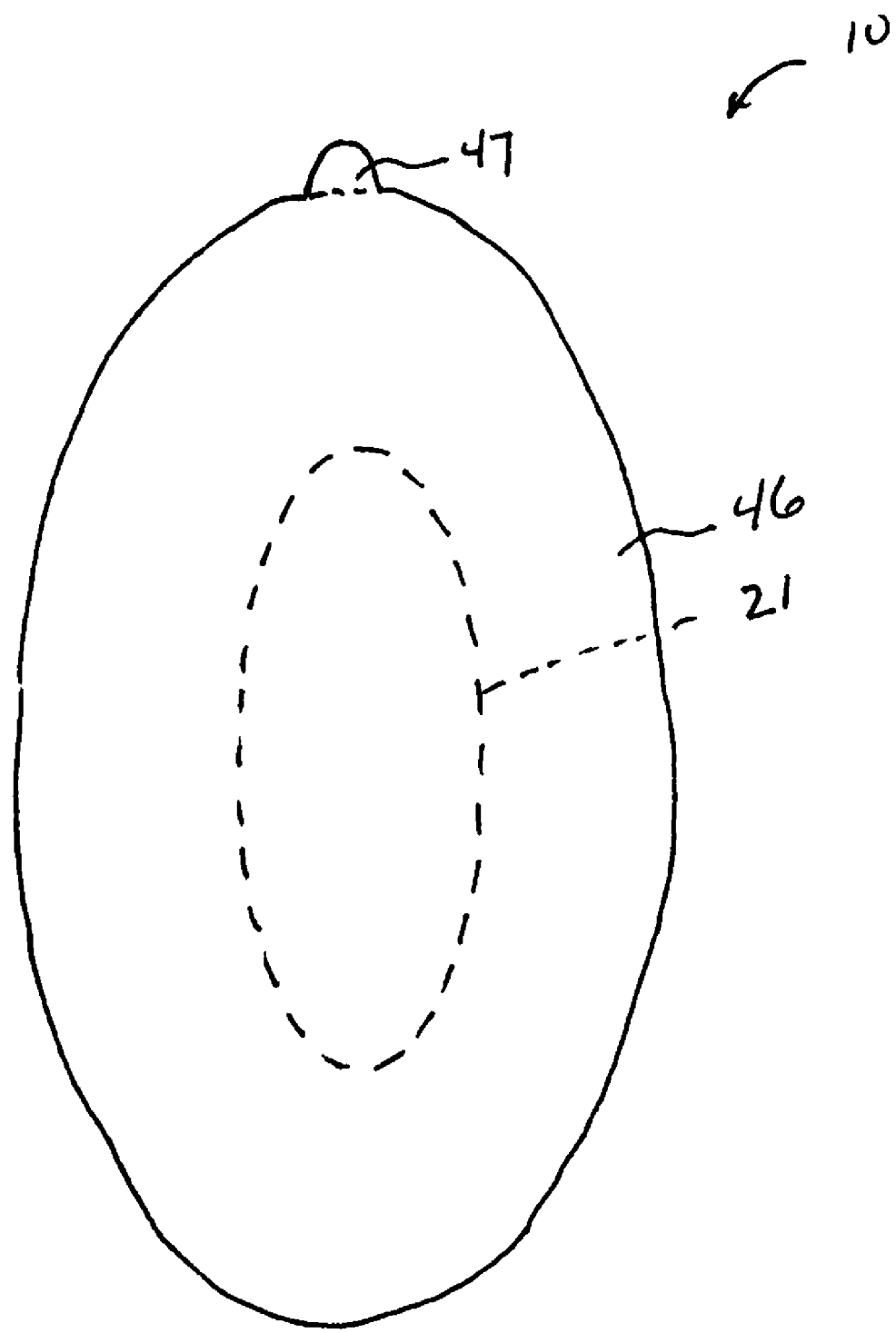

As is shown in FIGS. 8A and 8B, to protect the body adhesive 44, a peel sheet or release sheet 46 may be used to prevent the body adhesive 44 from becoming contaminated, thus loosing its ability to stick to the body of an user and/or prematurely adhering to an unintended surface. Suitable materials for use as a peel strip 46 are well known in the art and are commercially available. Examples of suitable peel sheets or release sheets include, a silicone coated Kraft paper, a silicone coated film or the like. Other release coating includes coating containing polytetrafluoroethylene. The peel sheet or release sheet 46 may extend beyond one or both of the ends and/or sides of the shell, as shown in FIG. 8B. Alternatively, the release sheet 46 may be sized to only cover the body adhesive on the first area 11 of the shell 14, as is shown in FIG. 8A. In yet another embodiment of the present invention, release sheet may extend beyond the adhesive at one or more locations, such as one of the ends or one of the sides of the shell as is shown in FIG. 8C by providing the release sheet 46 with a tab 47 for the user to grasp to remove the release sheet 46 from the absorbent article 10 and the body adhesive 44 on the absorbent article. When the release sheet 46 extends beyond the adhesive, it is generally easier for the user to remove the release sheet 46 to place the absorbent article 10 for use.

Alternatively, the release sheet 46 may be provided with a pressure sensitive adhesive to hold the release sheet 46 in place when the absorbent article is devoid of an adhesive for body attachment. In this configuration, the release sheet serves to protect the absorbent structure and first side of the shell from dirt and damage prior to use.

In another alternative, a release sheet may not be necessary. For example, the absorbent article may be rolled, folded onto itself or stacked upon each other. In these configurations, a release sheet is not needed. If rolled, the body adhesive 44 will generally contact the second side 17 of the shell 14. The body adhesive 44 should releasably stick to one second side of the shell by readily releasing when unrolled by the user or wearer. In addition, the body adhesive 44 should not leave a residue on the second side 17 of the shell. This should similarly occur when the absorbent articles 10 are stacked upon each other such that the body adhesive 44 of one article will attach the second side of the shell of a second article. In another possible configuration, the absorbent article may 10 be folded along the longitudinal axis 1 of the lateral axis such that the body adhesive 44 in one area comes into contact with body adhesive in another area. In the folded configuration, the body adhesive should be selected such that the body adhesive will release from itself when manipulated by a user.

The dimensions and shape of the shell 14 should be such that it is appropriately sized for its intended use. The same is true for the size and shape of the absorbent structure. Generally, the size and shape of the absorbent structure 21 will dictate the size of the shell 14. The shape of the shell 14 is selected so that the absorbent article will have a comfortable feeling for the user, which providing protection against leaks and preventing the absorbent article from becoming dislodged from the body of the user during user. Generally, the shell will be curved to fit the body of a user. The shell 14 also generally gives the absorbent article 10 its overall size and shape in the longitudinal 1 and lateral 2 directions.

When the absorbent article is intended for use as a pantiliner, a sanitary napkin or a feminine incontinence article, the shell 14 should be wider and longer than the absorbent structure 21 attached to the second area 12 of the shell 14. The absorbent structure should be at least as wide and as long as the labia majora of the user. As a result, to fit most women, the absorbent structure is longer in the longitudinal direction than it is wide in the lateral direction of the absorbent structure. Generally, for most women, the labia majora are generally between about 40 mm and about 70 mm in width and between about 80 mm and 150 mm in length. Ideally, the absorbent structure should be wider than the labia majora and slightly longer that the labia minora and slightly longer than or equal to the labia majora. Generally, the absorbent should be between about 40 mm and 90 mm in width in the lateral direction and between about 95 mm and about 150 mm in length the longitudinal direction. The shape of the absorbent structure 21 will generally tend to be oblong and may be an oval, a rectangle, tear drop shaped, hourglass shaped or racetrack shaped. As can be seen in FIGS. 1A, 5, 5B, 6,B,7 and 9, the absorbent structure 21 has a generally elliptical or oval shape to match the size and shape of the vaginal area of most women. An example of a teardrop shaped absorbent is shown in FIG. 1A.

Generally, the shape of the shell 14 may vary from a generally oval shape, as shown in FIGS. 1A and 1B to a shape which is a generally hourglass-like shape, shown in FIG. 5A. By generally hour glass shape, it is meant shape in which the sides 19 of the shell 14 converge towards one another at a point away along the longitudinal axis 1 of the shell 14 to form a narrowest portion 33 of the absorbent article. Generally, the hourglass-like shape provides a cut-out for the user's legs. By having an hourglass-like shape, the shell 14 will not be attached to the legs of a user during use. This will provide more comfort for the user of the absorbent article 10. The shape of the shell 14 should be selected such that the absorbent article 10 will be comfortable to wear, while providing very effective leakage protection to the user. The shell 14 and the absorbent structure 21 should be able to adapt to the curvature of a users body during use. Other possible shapes for the shell 14 are also shown in FIGS. 5, 5A, 5B, and 6A. Other shapes not specifically shown may also be used, provided that the shape will provide comfort to the user of the absorbent article.

To obtain an effective attachment of the absorbent article to the user, when the absorbent article is used as a sanitary napkin or an incontinence article, generally the width of the of the shell should be at least 10 mm on either side of the labia majora. Generally, the shell 14 of the absorbent article 10 will have a width, in the lateral direction 2, between about 50 mm up to 200 mm or more. Typically, the shell will be between about 60 and 120 mm at its narrowest point. This will allow the shell 14 to have a first area 11 that can be effectively attached to the skin of a user on either side of the labia majora.

Figure 9:
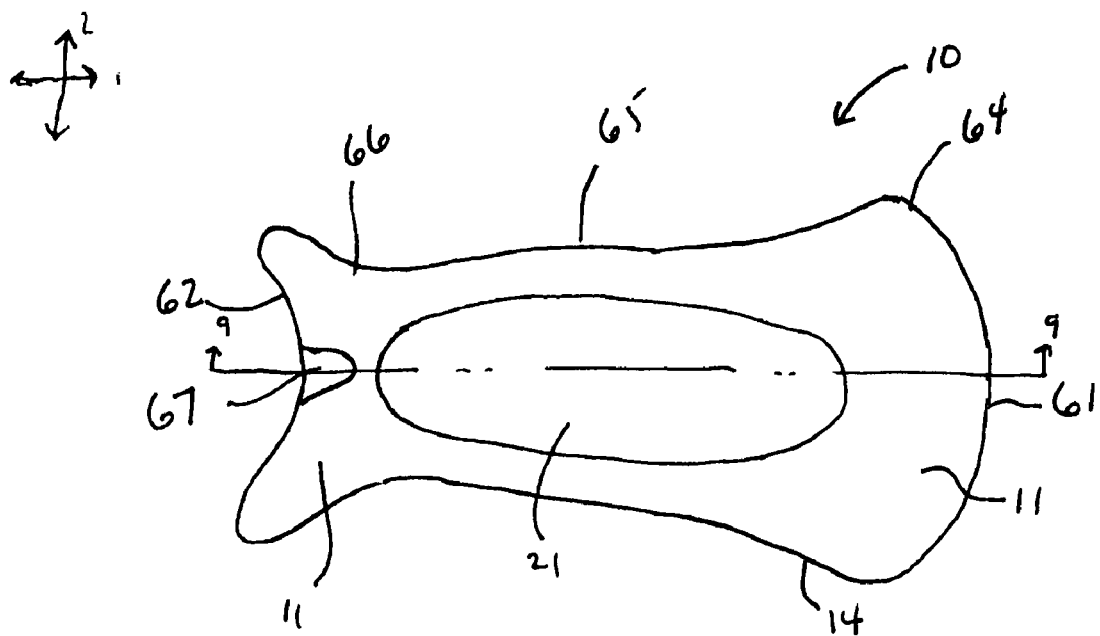
FIG. 9 shows a top view of another absorbent article of the present invention having a design for attachment to specific area of the body

In addition, the absorbent article 10 may also be configured to have an anterior portion 64, a central portion 65 and a posterior portion 66, as is shown in FIG. 9. As used herein, the term "anterior" refers to the direction towards the front of the wearer during use. As used herein, the term "posterior" refers to the direction towards the back of the wearer during use. A particular embodiment is shown in FIG. 8 of an absorbent article having a configuration designed to fit specific areas of the vulva region of a user. By providing specific portions for attachment to specific areas of the body of the user, the absorbent article may be configured to better fit the body of the user. The anterior portion 64 of the absorbent article will be the portion of the absorbent article between the absorbent structure 21 and the first end 61 of the absorbent article 10. The posterior portion 66 of the absorbent article 10 will be the portion of the absorbent article between the absorbent structure 21 and the second end 62 of the absorbent article 10. Generally, the posterior portion 66 will be designed to be placed between the vagina area and the anal area of the user. The anterior portion 64 is designed to be placed on the mons Veneris region of a female user. The central portion 65 of the absorbent article 10 is designed to cover the vagina area of the user and the skin area surround the lateral sides of the labia majora, when the absorbent article is used as a pantiliner, sanitary napkin or an incontinence article. In an alternative use, the absorbent article of the present invention may also be used as an underwear replacement, or a guard for a swimming suit.

Figure 10:
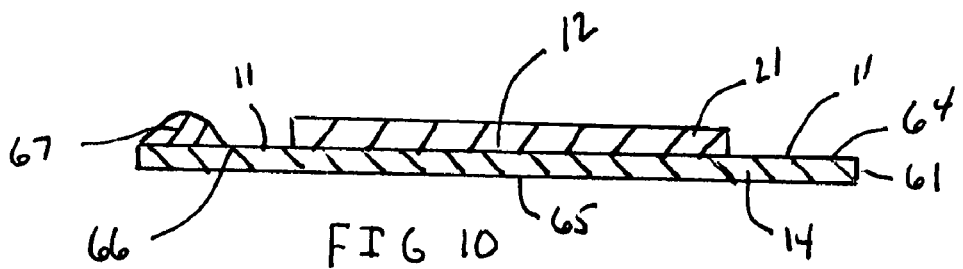
FIG. 10 shows a cross-section view of FIG. 9 along lines 9-9.

To obtain an effective attachment to the body of the user, the shell 14 can be configured to be anatomically correct for a user. As is shown in FIGS. 9 and 10, the shape of the absorbent article 10 is such that it will correctly and securely fit in the vulva region of a user. The general shape of the absorbent article shown in FIG. 10 has been found to effectively attach to the vulva region of female users of the absorbent article. Additional features may be included to ensure an anatomically correct shape. For example, in the posterior region of the absorbent article 10, more particularly, the posterior region of the shell on the first side 15, the shell 14 may be imparted with a three-dimensional protrusion 67, as shown in FIGS. 9 and 10. The protrusion 67 acts to fit comfortably in the perinea region of the user. The protrusion 67 may be formed from the shell material of may be formed from the body adhesive 44. By providing the three-dimensional protrusion 67, the absorbent article can effective fit to the typical body shape of the female user, thereby preventing leaks form the posterior portion of the absorbent article. The protrusion 67 may also serve as a guide to the user in placement of the absorbent article 10 on the body prior to use.

Figure 11:
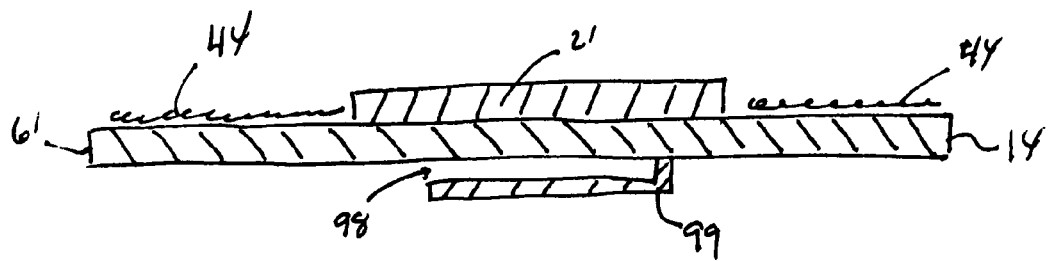
FIG. 11A and FIG. 11B shown embodiments of the present invention with placement guides.
Figure 11:
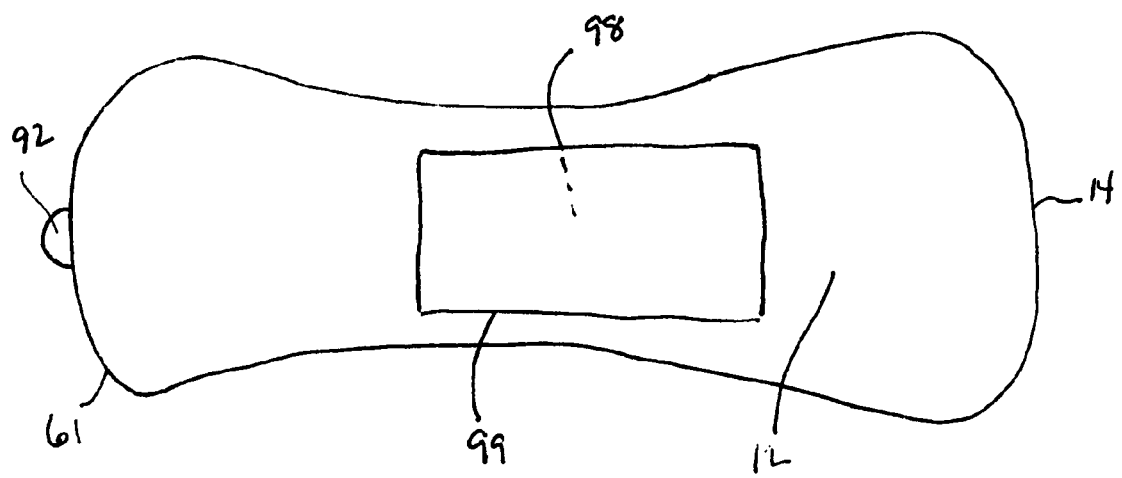

The absorbent article of the present invention may have other features which aid the user to place and remove the absorbent article from the body. As is shown in FIGS. 10A and 10B, the second side 12 of the shell 14 may be provided with positioning aids such as a finger pocket 99, shown in FIGS. 11A and 11B, or finger grooves in the shell material, as is shown in FIG. 11B. The finger pocket 99 has an opening 98 towards the anterior portion 64 or first end 61 of the absorbent article 10. The pocket 99 gives the user a location to place her fingers during placement of the absorbent article 10 onto the user's body. The pocket 99 may be an opening wide enough for the user to place at least two fingers in the pocket. Alternatively, may be two or more openings which allows the user to place only one finger in each opening. Other similar positioning aids may be used to help guide a user to properly place the absorbent article for use. For example, grooves may be placed in the second side 12 of the shell 14 opposite the absorbent structure. This may allow the user to feel the location of the absorbent structure relative to the vulva region during application of the absorbent article 10 to the vulva region of the body. The pocket 99 may also assist the user in removing the absorbent article from their body.

The absorbent article 10 may also be provided with a removal aid which provides the user with an easy way to grasp and remove the absorbent article applied to the body. One particular removal aid is shown in FIG. 10B including a tab 92 located on the first end 61 of the shell which is not adhered to the body or is devoid of adhesive. Alternatively, other removal aids, such as having an area of the first end 61 being devoid of the body attaching adhesive 44. Other types of removal aid which may be present include loops, and pull strings. The removal aid allows the user to effectively begin the process of gentling removing the absorbent article from the body of the user, without the need of having to find a portion of the shell which may not be completely attached.

Other features or additives may be incorporated into the absorbent article of the present invention. For example, the absorbent article may contain an odor control agent, or a fragrance, skin wellness agents and other similar additives currently used in currently available absorbent articles. Any odor control agent or, fragrance known to those skilled in the art may be used in the absorbent article of the present invention. The odor control agent or fragrance may be added in various components of the absorbent article, including the shell 14, the absorbent structure 21 of the body adhesive 44. Skin wellness additives may be added onto the absorbent structure, any portion of the first area 15 of the shell not attached to the user or in the body adhesive 44.

Generally, to apply the absorbent article 10 to the body of a user, the release sheet 46, protecting the absorbent structure and adhesive, if present, is removed from first surface of the shell. Next, the user positions the absorbent structure of the portion of the body in which absorbency is needed. If positioning pockets or other positioning aids are present on the absorbent structure, the user may optionally use these positioning aids to properly place the absorbent article for use. In the case of sanitary napkins and incontinence absorbent articles for females, the absorbent is positioned over the vagina area such that the absorbent structure will absorb body fluids. The user then checks to ensure that the first area 11 of the shell or the adhesive 44, if present, is contacting the skin around the vagina area.

If the absorbent article is intended to have a front and a back portion, the user first identifies the anterior portion 64 and/or the posterior portion 66 of the absorbent article. To aid in identification of the anterior and posterior portions, indicia located on the release sheet, shell or absorbent to indicate the anterior portion and/or posterior portion of the absorbent article may be present. Indicia can be simply lettering or a picture to indicate the front or back of the absorbent article. Once anterior portion and posterior portion are identified by the user, the user places the absorbent article in the same manner described above.

In each case, the absorbent structure, which is designed to cover the labia majora of the user, may be positioned with the aid of the absorbent structure. More specifically, the absorbent structure, when sized and shaped to the approximate size of the labia majora, can serve to guide the placement of the absorbent structure over the labia majora. Once properly placed, pressure is applied by the user to the second surface of the shell which will allow the first surface of the shell to contact the skin of the user, or to allow any adhesive applied to the first surface to be applied to the skin of the user.

By having the absorbent article 10 attached to the body of a user, the absorbent article 10 will tend to move with the skin of the user. This results in a comfortable to wear absorbent article which will be less likely to leak than conventional absorbent articles. The absorbent article has a very close to the body fit which may provide improved discretion for the user.

Other benefits of the absorbent article 10 of the present invention may also be provided. For example, when the first side of the shell has an adhesive applied thereto, upon removal of the absorbent article after user, the user may fold the first side of the shell onto itself to dispose of the used absorbent article. An effective seal may be formed around the perimeter of the shell, thereby effectively encapsulating the absorbent structure within a closure. As a result, any odors associated with the absorbed fluids will be contained within the shell material.

Although the present invention has been described with reference to various embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

The invention claimed is:

1. An absorbent article for attachment to a wearer's skin in the vulva region of the wearer's torso, said article comprising:
   a shell having a first side and a second side, the first side having a first area and a second area, wherein the first area surrounds a majority of the second area, and wherein the first side is adapted to be the body facing side of the absorbent article and the second side is adapted to be the garment facing side of the absorbent article wherein the shell comprises a laminate of a woven or a nonwoven web with a sheet of a silicone polymer; and
   an absorbent structure attached to the first side and located entirely within the second area of the shell, the absorbent structure comprising an absorbent material;
   wherein when applied to the wearer the first area of the shell is configured to contact the wearer's skin surrounding the vulva region and the shell is sized and shaped such that the first area is configured to only contact the skin of the wearer proximate to the vulva region; and wherein the first area of the shell comprises the sheet of silicone polymer having adhesive properties, wherein the adhesive properties are adapted to attach directly to the wearer's vulva region.

2. The absorbent article according to claim 1, wherein the second area of the shell has a second area circumference, the first area of the shell surrounds at least 75% of the second area circumference.

3. The absorbent article according to claim 2, wherein the first area of the shell surrounds at least 95% of the second area circumference.

4. The absorbent article according to claim 1, wherein the shell comprises a silicone material and is translucent.

5. The absorbent article according to claim 1, wherein the shell comprises a silicone material which part of an interpenetrating polymer network.

6. The absorbent article according to claim 1, wherein the first area of the shell comprises an adhesive applied thereto.

7. The absorbent article according to claim 6, wherein the first area is essentially entirely covered by the adhesive.

8. The absorbent article according to claim 1, wherein the adhesive properties are imparted to the first area of the shell by the physical properties of materials used to prepare the shell.

9. The absorbent article according to claim 1, wherein the shell has a three-dimensional concave shape such that the first side of the shell is an inward curving surface.

10. The absorbent article according to claim 1, further comprising an anterior portion and a posterior portion, wherein the posterior portion is adapted to attach to the body of a user between the vulva region and the anal region of the body of the user and the anterior portion is adapted to attach to the mons Veneris region of a user.

11. The absorbent article according to claim 10, wherein the shell has an anatomically correct shape for placement in the vulva region of a user.

12. The absorbent article according to claim 11, wherein the posterior portion further comprises a protrusion extending upward from the first side of the shell.

13. The absorbent article according to claim 1, wherein the shell is breathable.

14. The absorbent article according to claim 1, wherein the absorbent structure is contained within the shell material.

15. The absorbent article according to claim 1, wherein the absorbent structure is attached to the shell material.

16. The absorbent article according to claim 15, wherein the absorbent structure is sized and shaped to cover the labia majora of a user.

17. The absorbent article according to claim 15, wherein the absorbent structure comprises an absorbent core and a body side liner, wherein the absorbent core has an edge and is positioned between the body side liner and the shell and wherein the body side liner only extends to the edge of the absorbent core.

18. The absorbent article according to claim 1, further comprising a release sheet attached to the first side of the shell.

19. The absorbent article according to claim 1, further comprising a removal aid.

20. The absorbent article according to claim 1, further comprising a placement aid.

21. The absorbent article according to claim 1, wherein the absorbent article comprises a sanitary napkin.

22. The absorbent article according to claim 1, wherein the absorbent article comprises an incontinence absorbent article.

23. The absorbent article according to claim 1, wherein the absorbent structure is integrated into the shell.

24. The absorbent article according to claim 1, wherein a portion of the absorbent structure is located over the shell.

25. The absorbent article according to claim 24, wherein the absorbent structure further comprises a liquid impermeable layer.

26. The absorbent article according to claim 1 wherein the adhesive properties are confined to the first area.

\* \* \* \* \*